(12) United States Patent
Tomita et al.

(10) Patent No.: US 11,957,906 B2
(45) Date of Patent: Apr. 16, 2024

(54) EXTERNAL STIMULUS APPLICATION SYSTEM, EXTERNAL STIMULUS CONDITION DETERMINATION SYSTEM, AND EXTERNAL STIMULUS CONDITION DETERMINATION SUPPORT SERVER

(71) Applicant: Mitsui Chemicals, Inc., Tokyo (JP)

(72) Inventors: Hidetoshi Tomita, Yokohama (JP); Yuki Kondo, Ichihara (JP); Motoyasu Yasui, Chiba (JP); Kenji Iida, Düsseldorf (DE)

(73) Assignee: Mitsui Chemicals, Inc., Tokyo (JP)

( * ) Notice: Subject to any disclaimer, the term of this patent is extended or adjusted under 35 U.S.C. 154(b) by 660 days.

(21) Appl. No.: 17/043,757

(22) PCT Filed: Mar. 27, 2019

(86) PCT No.: PCT/JP2019/013088
§ 371 (c)(1),
(2) Date: Sep. 30, 2020

(87) PCT Pub. No.: WO2019/189306
PCT Pub. Date: Oct. 3, 2019

(65) Prior Publication Data
US 2021/0138240 A1 May 13, 2021

(30) Foreign Application Priority Data
Mar. 30, 2018 (JP) .................. 2018-068923

(51) Int. Cl.
*A61N 1/36* (2006.01)
*A61N 1/04* (2006.01)

(52) U.S. Cl.
CPC ....... *A61N 1/36003* (2013.01); *A61N 1/0452* (2013.01); *A61N 1/36031* (2017.08)

(58) Field of Classification Search
CPC .............. A61N 1/36003; A61N 1/0452; A61N 1/36031
See application file for complete search history.

(56) References Cited

U.S. PATENT DOCUMENTS

2008/0208288 A1* 8/2008 Gesotti .............. A61N 1/36003
607/48
2010/0041959 A1 2/2010 Hiroyasu
(Continued)

FOREIGN PATENT DOCUMENTS

JP 0722264 U 4/1995
JP 2002-331007 A 11/2002
(Continued)

OTHER PUBLICATIONS

International Search Report from International Application No. PCT/JP2019/013088, dated Jun. 25, 2019.

*Primary Examiner* — Amanda K Hulbert
*Assistant Examiner* — Philip C Edwards
(74) *Attorney, Agent, or Firm* — Shih IP Law Group, PLLC.

(57) ABSTRACT

This external stimulus application system is structured so as to comprise: an external stimulus unit that applies an external stimulus to a target area of a user's body; a detection unit that detects changes in a detected area of the user's body during an action of the user; a control unit that causes the external stimulus unit to produce a stimulus if a detected value detected by the detection unit satisfies a prescribed condition; and a storage unit that stores the detected value.

17 Claims, 15 Drawing Sheets

(56) References Cited

U.S. PATENT DOCUMENTS

| | | | |
|---|---|---|---|
| 2013/0123568 A1* | 5/2013 | Hamilton | ............... A61N 2/02 600/13 |
| 2014/0094345 A1 | 4/2014 | Kim | |
| 2015/0265834 A1* | 9/2015 | Glukhovsky | ........ A61B 5/4851 607/49 |
| 2016/0220813 A1 | 8/2016 | Edgerton | |
| 2017/0036019 A1 | 2/2017 | Matsushita | |

FOREIGN PATENT DOCUMENTS

| | | |
|---|---|---|
| JP | 2004-081676 A | 3/2004 |
| JP | 2008-125888 A | 6/2008 |
| JP | 2012-011102 A | 1/2012 |
| JP | 2014509919 A | 4/2014 |
| JP | 2017-153822 A | 9/2017 |
| KR | 10-2018-0089127 A | 8/2018 |
| WO | 20160007885 A1 | 1/2016 |
| WO | 2016/143145 A | 9/2016 |

\* cited by examiner

| | AVERAGE IN 1ST DAY (WALKING ON LEVEL GROUND) | AVERAGE IN 2ND DAY (WALKING ON LEVEL GROUND) | ... | AVERAGE IN 7TH DAY (WALKING ON LEVEL GROUND) | ... | AVERAGE IN 30TH DAY (WALKING ON LEVEL GROUND) |
|---|---|---|---|---|---|---|
| STRIDE LENGTH (RIGHT) | 45cm | 46cm | | 49cm | | 55cm |
| STRIDE LENGTH (LEFT) | 47cm | 48cm | | 50cm | | 55cm |
| PERIOD | 0.3sec | 0.3sec | | 0.4sec | | 0.6sec |
| ADDUCTION (TWIST ANGLE) | 10° | 9° | | 7° | | 3° |
| MUSCLE STRENGTH | 40%MVC | 41%MVC | | 45%MVC | | 50%MVC |
| WEARING TIME | 7hrs | 16hrs | | 10hrs | | 8hrs |

| USER INFORMATION | | INFORMATION REGARDING MOTION | | VIBRATION CONDITION (VIBRATION FREQUENCY) |
|---|---|---|---|---|
| AGE | GENDER | TYPE OF EXERCISE | STRENGTH OF EXERCISE | |
| 40 YEARS OLD | MALE | WALKING | STRONG | 40Hz |
| | | | WEAK | 50Hz |
| 50 YEARS OLD | MALE | WALKING | STRONG | 50Hz |
| | | | WEAK | 60Hz |
| 60 YEARS OLD | MALE | WALKING | STRONG | 60Hz |
| | | | WEAK | 70Hz |
| 70 YEARS OLD | MALE | WALKING | STRONG | 70Hz |
| | | | WEAK | 80Hz |
| 80 YEARS OLD | MALE | WALKING | STRONG | 80Hz |
| | | | WEAK | 90Hz |

FIG. 11A

| | | 1ST DAY AFTER INJURY (WALKING ON LEVEL GROUND) | 2ND DAY AFTER INJURY (WALKING ON LEVEL GROUND) | ... | 8TH DAY AFTER INJURY (WALKING ON LEVEL GROUND) | ... | 15TH DAY AFTER INJURY (WALKING ON LEVEL GROUND) |
|---|---|---|---|---|---|---|---|
| INFORMATION REGARDING MOTION | TYPE OF EXERCISE | WALKING | WALKING | ... | WALKING | ... | WALKING |
| FIRST INFORMATION OR SECOND INFORMATION | STRENGTH OF EXERCISE | WEAK | WEAK | | WEAK | | WEAK |
| | STRIDE LENGTH (RIGHT) | 30cm | 35cm | | 45cm | | 55cm |
| | STRIDE LENGTH (LEFT) | 47cm | 48cm | | 50cm | | 55cm |
| | PERIOD | 0.25sec | 0.25sec | | 0.4sec | | 0.6sec |
| | PERIOD (RIGHT) | 0.2sec | 0.3sec | | 0.4sec | | 0.6sec |
| | PERIOD (LEFT) | 0.3sec | 0.3sec | | 0.4sec | | 0.6sec |
| | WALKING SPEED | 30m/min | 35m/min | | 40m/min | | 55m/min |
| | KNEE BENDING ANGLE (RIGHT) | 30° | 35° | | 45° | | 60° |
| | KNEE BENDING ANGLE (LEFT) | 60° | 60° | | 60° | | 60° |
| | ADDUCTION (TWIST ANGLE) | 10° | 9° | | 7° | | 3° |
| | MUSCLE STRENGTH | 40%MVC | 41%MVC | | 45%MVC | | 50%MVC |
| | WEARING TIME | 7hrs | 16hrs | | 10hrs | | 8hrs |
| VIBRATION CONDITION | | 50Hz | 50Hz | | 50Hz | | 50Hz |
| PARAMETER SET BY DOCTOR | | −2 | − | | 0 | | +1 |

FIG. 11B

| USER INFORMATION | | INFORMATION REGARDING MOTION | | ELECTRICAL STIMULUS CONDITION (FREQUENCY) |
|---|---|---|---|---|
| AGE | GENDER | TYPE OF EXERCISE | STRENGTH OF EXERCISE | |
| 40 YEARS OLD | MALE | WALKING | STRONG | 16Hz |
| | | | WEAK | 8Hz |
| 50 YEARS OLD | MALE | WALKING | STRONG | 16Hz |
| | | | WEAK | 8Hz |
| 60 YEARS OLD | MALE | WALKING | STRONG | 16Hz |
| | | | WEAK | 8Hz |
| 70 YEARS OLD | MALE | WALKING | STRONG | 16Hz |
| | | | WEAK | 8Hz |
| 80 YEARS OLD | MALE | WALKING | STRONG | 16Hz |
| | | | WEAK | 8Hz |

FIG. 11C

| | | 1ST DAY AFTER INJURY (WALKING ON LEVEL GROUND) | 2ND DAY AFTER INJURY (WALKING ON LEVEL GROUND) | ... | 8TH DAY AFTER INJURY (WALKING ON LEVEL GROUND) | ... | 15TH DAY AFTER INJURY (WALKING ON LEVEL GROUND) |
|---|---|---|---|---|---|---|---|
| INFORMATION REGARDING MOTION | TYPE OF EXERCISE | WALKING | WALKING | | WALKING | | WALKING |
| | STRENGTH OF EXERCISE | STRONG | STRONG | | STRONG | | STRONG |
| FIRST INFORMATION OR SECOND INFORMATION | STRIDE LENGTH (RIGHT) | 30cm | 35cm | | 45cm | | 55cm |
| | STRIDE LENGTH (LEFT) | 47cm | 48cm | | 50cm | | 55cm |
| | PERIOD | 0.25sec | 0.25sec | | 0.4sec | | 0.6sec |
| | PERIOD (RIGHT) | 0.2sec | 0.3sec | | 0.4sec | | 0.6sec |
| | PERIOD (LEFT) | 0.3sec | 0.3sec | | 0.4sec | | 0.6sec |
| | WALKING SPEED | 30m/min | 35m/min | | 40m/min | | 55m/min |
| | KNEE BENDING ANGLE (RIGHT) | 30° | 35° | | 45° | | 60° |
| | KNEE BENDING ANGLE (LEFT) | 60° | 60° | | 60° | | 60° |
| | ADDUCTION (TWIST ANGLE) | 10° | 9° | | 7° | | 3° |
| | MUSCLE STRENGTH | 40%MVC | 41%MVC | | 45%MVC | | 50%MVC |
| | WEARING TIME | 7hrs | 16hrs | | 10hrs | | 8hrs |
| ELECTRICAL STIMULUS CONDITION | | 16Hz | 16Hz | | 16Hz | | 16Hz |
| PARAMETER SET BY DOCTOR | | -2 | -1 | | 0 | | +1 |

FIG. 11D

EXTERNAL STIMULUS APPLICATION SYSTEM, EXTERNAL STIMULUS CONDITION DETERMINATION SYSTEM, AND EXTERNAL STIMULUS CONDITION DETERMINATION SUPPORT SERVER

TECHNICAL FIELD

The present invention relates to an external stimulus application system, an external stimulus condition determination system, an external stimulus condition determination support server, and a data structure.

BACKGROUND ART

Hitherto, an apparatus that applies an external stimulus, such as a vibratory stimulus or an electrical stimulus, to a target area of a user's body has been used in rehabilitation after injury or surgery with intent to realize relief of symptoms, promotion of healing, higher efficiency of treatment, strengthening of muscles, or the like.

Patent Literature (hereinafter, abbreviated as PTL) 1 discloses an apparatus that applies a vibratory stimulus to a target area of a user for the purpose of improving symptoms, such as arthritis and muscle stiffness. PTL 2 discloses an apparatus that applies an electrical stimulus to a target area of a user for the purpose of strengthening muscles.

CITATION LIST

Patent Literature

PTL 1
Japanese Examined Utility Model (Registration) Application Publication No. H7-22264
PTL 2
WO2016/143145

SUMMARY OF INVENTION

Technical Problem

In the apparatuses disclosed in PTL 1 and PTL 2, a vibrator or an electrode section applies the intermittent vibratory stimulus or electrical stimulus to the target area of the user's body with intent to improve the above-mentioned symptoms. However, the apparatuses disclosed in PTL 1 and PTL 2 cannot store information regarding the vibratory stimulus or the electrical stimulus that have been applied to users.

An object of the present invention is to provide an external stimulus application system that can store a value detected by a detection section, and to further provide an external stimulus condition determination system, an external stimulus condition determination support server, and a data structure.

Solution to Problem

An external stimulus application system according to the present invention includes: an external stimulation section that applies an external stimulus to a target area in a body of a user; a detection section that detects first information during a motion of the user, the first information being information regarding change in a detected area in the body of the user; a control section that causes the external stimulation section to generate the stimulus when the first information satisfies a predetermined condition; and a storage section that stores a value detected by the detection section.

An external stimulus condition determination system according to the present invention determines an external stimulus condition in an external stimulus application apparatus applying an external stimulus to a target area of a user. This external stimulus condition determination system includes: a storage section that stores the external stimulus condition regarding the external stimulus in advance; an external stimulus condition obtaining section that, when user information regarding the user and information regarding a motion performed by the user are input, obtains the external stimulus condition corresponding to the input user information and the input information regarding the motion from the storage section; and an output section that sends the external stimulus condition obtained by the external stimulus condition obtaining section to the external stimulus application apparatus.

An external stimulus condition determination support server according to the present invention is communicatively connected to an external stimulus application apparatus applying an external stimulus to a target area of a user. This external stimulus condition determination support server includes: a storage section that stores an external stimulus condition regarding the external stimulus in advance; an external stimulus condition obtaining section that receives user information regarding the user and information regarding a motion performed by the user from a terminal that is communicatively connected to the external stimulus condition determination support server, and obtains the external stimulus condition corresponding to the received user information and the received information regarding the motion from the storage section; and an output section that sends the external stimulus condition obtained by the external stimulus condition obtaining section to the external stimulus application apparatus.

A data structure according to the present invention is a data structure for use in an external stimulus condition determination support server that is communicatively connected to an external stimulus application apparatus applying an external stimulus to a target area of a user. This data structure includes an external stimulus condition that is made in correspondence with user information regarding the user and information regarding a motion performed by the user. The data structure is used by the external stimulus condition determination support server to execute processing of: receiving the user information and the information regarding the motion; obtaining the external stimulus condition corresponding to the received user information and the received information regarding the motion; and sending the obtained external stimulus condition to the external stimulus application apparatus.

Advantageous Effects of Invention

The present invention can provide the external stimulus application system that can store the value detected by the detection section, and can further provide the external stimulus condition determination system, the external stimulus condition determination support server, and the data structure.

BRIEF DESCRIPTION OF DRAWINGS

FIG. 11A is a conceptual view illustrating a data structure stored in a server-side storage section;

FIG. 11B is a conceptual view illustrating a data structure stored in the server-side storage section;

FIG. 11C is a conceptual view illustrating a data structure stored in the server-side storage section;

FIG. 11D is a conceptual view illustrating a data structure stored in the server-side storage section.

DESCRIPTION OF EMBODIMENTS

Embodiments of the present invention will be described in detail below with reference to the accompanying drawings.

Embodiment 1

Figure 1:
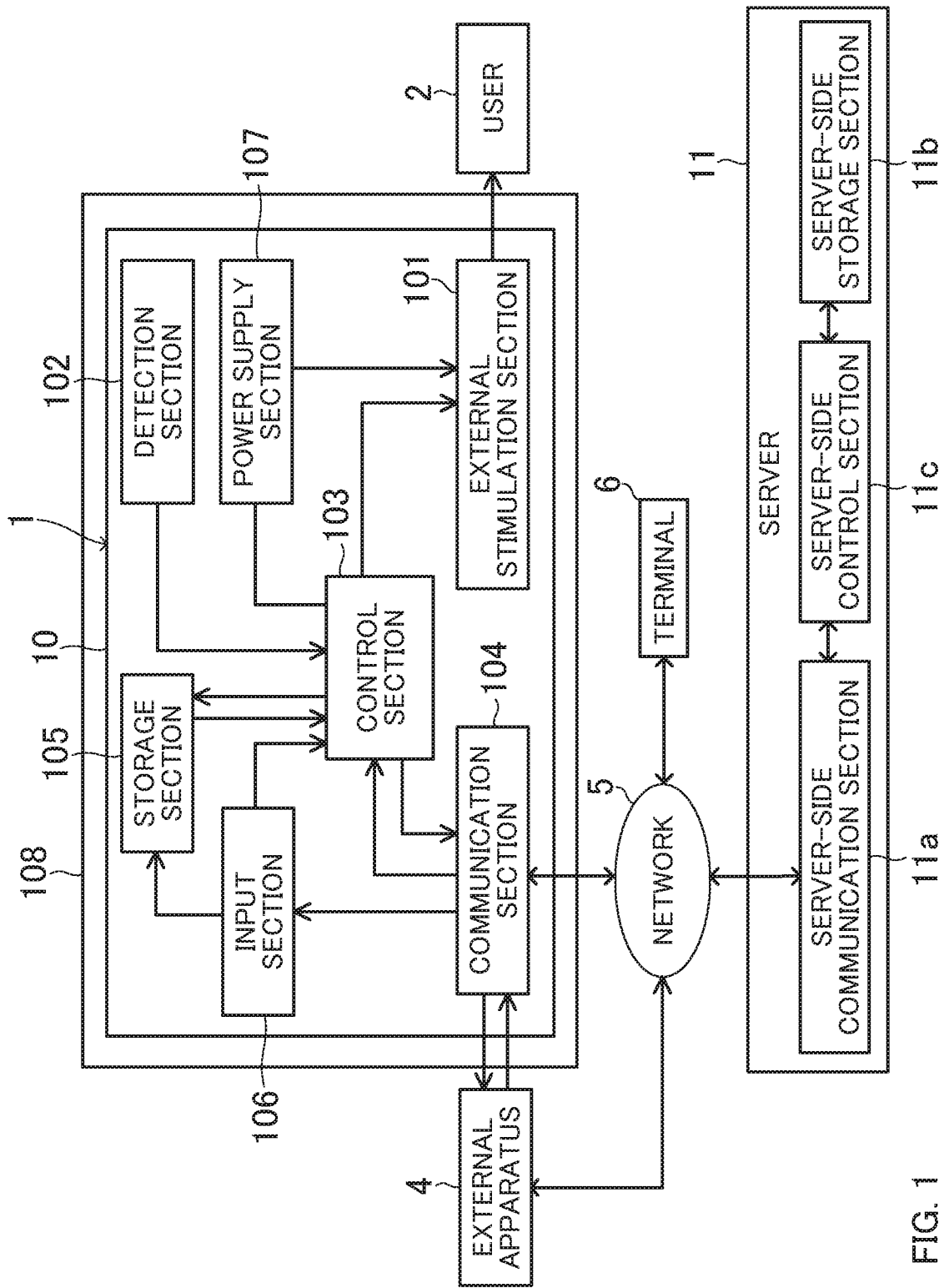
FIG. 1 is a block diagram illustrating an external stimulus application apparatus according to Embodiment 1 of the present invention.

FIG. 1 is a block diagram illustrating external stimulus application system 1 according to Embodiment 1 of the present invention.

<External Stimulus Application System>

External stimulus application system 1 according to this embodiment will be described below with reference to FIG. 1. External stimulus application system 1 includes external stimulus application apparatus 10 and server 11.

<External Stimulus Application Apparatus>

First, external stimulus application apparatus 10 is described. External stimulus application apparatus 10 according to this embodiment applies, during a motion of user 2 (see FIGS. 2 and 6), an external stimulus to a target area (for example, vastus medialis muscle 203, see FIG. 2) of the body of user 2. In an example, external stimulus application system 1 according to this embodiment includes external stimulus application apparatus 10 that applies a vibratory stimulus as the external stimulus. External stimulus application system 1 may alternatively or additionally include an electrical stimulus application apparatus (electrical stimulation section) or an electrode section (not illustrated) that applies, as the external stimulus, an electrical stimulus to the target area of the body of user 2, thus contracting the muscle. In this Description, external stimulus application apparatus 10 may be read as a vibratory stimulus application apparatus. In this Description, external stimulus application apparatus 10 may be read as the electrical stimulus application section or the electrode section as appropriate. Furthermore, in this Description, the external stimulus may be read as the vibratory stimulus or the electrical stimulus as appropriate.

External stimulus application apparatus 10 includes external stimulation section 101, detection section 102, control section 103, communication section 104, storage section 105, input section 106, power supply section 107, and wearing section 108.

<External Stimulation Section>

External stimulation section 101 applies the external stimulus to the target area of the body of user 2 under control of control section 103 described later. External stimulation section 101 is held by wearing section 108 described later. In use, external stimulation section 101 is arranged in the state directly or indirectly contacting a surface of the target area of user 2 (hereinafter referred to as an "external stimulus applied surface").

FIGS. 3A to 3G illustrate practical examples of the external stimulation section. External stimulation sections 101A to 101G illustrated respectively in FIGS. 3A to 3G will be described below in order.

<First Example of External Stimulation Section>

Figure 3A:
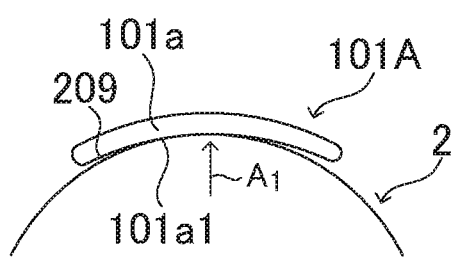
FIG. 3A is a schematic view illustrating a first example of an external stimulation section.

FIG. 3A is a schematic view illustrating a first example of the external stimulation section. External stimulation section 101A illustrated in FIG. 3A includes housing 101a that has a shape to follow external stimulus applied surface 209 of user 2. An eccentric motor (not illustrated) is installed in housing 101a. Thus, in this example, the external stimulus is the vibratory stimulus. The first example of the external stimulation section according to this example may be regarded as a first example of a vibratory stimulation section. The electrical stimulus may be used as the external stimulus by providing an electrode section while the configuration of the housing 101a in this example is adopted in the external stimulation section. In such a case, the first example of the external stimulation section according to this example may be regarded as a first example of an electrical stimulation section. The above point is similarly applied to second to seventh examples described later.

Housing 101a has external stimulus applying surface 101a1 in one surface (namely, in a surface positioned to face external stimulus applied surface 209). External stimulus applying surface 101a1 is a concave surface shaped to follow external stimulus applied surface 209. The shape of external stimulus applying surface 101a1 is not limited to the illustrated one. The size, the curvature, and so on of external stimulus applying surface 101a1 may be determined as appropriate in conformity with the shape of external stimulus applied surface 209.

In this example, the other surface (namely, a surface on the opposite side to external stimulus applying surface 101a1) of housing 101a is a convex surface having the same curvature as that of external stimulus applying surface 101a1. The shape of the other surface of housing 101a is not limited to the one illustrated in this example.

In this example, since a large area of external stimulus applying surface 101a1 can be obtained, contact pressure in a contact region between external stimulus applying surface 101a1 and user 2 can be reduced.

<Second Example of External Stimulation Section>

Figure 3B:
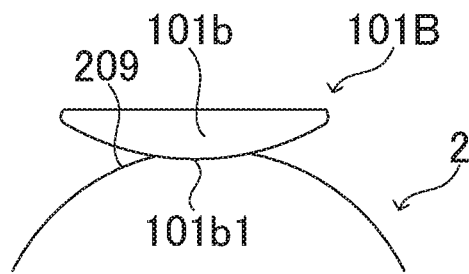
FIG. 3B is a schematic view illustrating a second example of the external stimulation section.

FIG. 3B is a schematic view illustrating a second example of the external stimulation section. External stimulation section 101B illustrated in FIG. 3B includes housing 101b. An eccentric motor (not illustrated) is installed in housing 101b.

Housing 101b has external stimulus applying surface 101b1 in one surface (namely, in a surface positioned to face external stimulus applied surface 209). External stimulus applying surface 101b1 is a convex surface projecting toward external stimulus applied surface 209. The shape of external stimulus applying surface 101b1 is not limited to the illustrated one. The size, the curvature, and so on of external stimulus applying surface 101b1 may be determined as appropriate in conformity with the shape of external stimulus applied surface 209.

The other surface (namely, a surface on the opposite side to external stimulus applying surface 101b1) of housing 101b is a flat surface. The shape of the other surface of housing 101b is not limited to the one illustrated in this example.

<Third Example of External Stimulation Section>

Figure 3C:
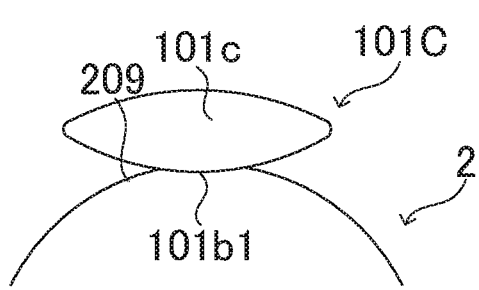
FIG. 3C is a schematic view illustrating a third example of the external stimulation section.

FIG. 3C is a schematic view illustrating a third example of the external stimulation section. In external stimulation section 101C illustrated in FIG. 3C, the other surface (namely, a surface on the opposite side to external stimulus applying surface 101b1) of housing 101c is different from that in external stimulation section 101B illustrated in FIG. 3B.

In this example, since external stimulus applying surface 101b1 is the convex surface, the external stimulus can be accurately applied to the target area.

<Fourth Example of External Stimulation Section>

Figure 3D:
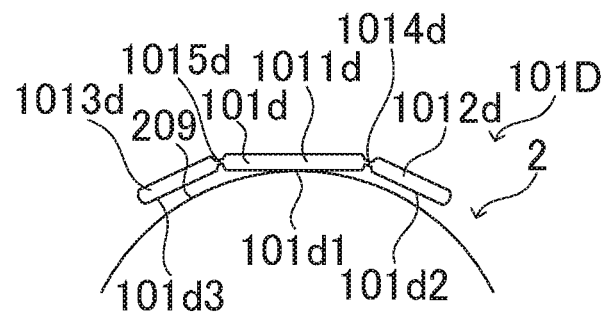
FIG. 3D is a schematic view illustrating a fourth example of the external stimulation section.

FIG. 3D is a schematic view illustrating a fourth example of the external stimulation section. External stimulation section 101D illustrated in FIG. 3D includes housing 101d. Housing 101d includes first housing element 1011d, second housing element 1012d, and third housing element 1013d.

First housing element 1011d is arranged at a center of housing 101d. First housing element 1011d has a substantially rectangular box-like shape. First housing element 1011d has external stimulus applying surface 101d1 in one surface (surface positioned to face external stimulus applied surface 209). External stimulus applying surface 101d1 is a flat surface. The shape of external stimulus applying surface 101d1 is not limited to the illustrated one. For example, external stimulus applying surface 101d1 may be a concave surface shaped to follow external stimulus applied surface 209 or a convex surface projecting toward external stimulus applied surface 209.

In this example, the other surface (namely, a surface on the opposite side to external stimulus applying surface 101d1) of first housing element 1011d is a flat surface. The shape of the other surface of first housing element 1011d is also not limited to the illustrated one.

Second housing element 1012d and third housing element 1013d have a substantially rectangular box-like shape. Second housing element 1012d and third housing element 1013d are arranged with first housing element 1011d sandwiched between them.

Second housing element 1012d and third housing element 1013d have respectively external stimulus applying surfaces 101d2 and 101d3 in one surfaces (surfaces positioned to face external stimulus applied surface 209). External stimulus applying surfaces 101d2 and external stimulus applying surface 101d3 are flat surfaces. The shapes of external stimulus applying surfaces 101d2 and external stimulus applying surface 101d3 are not limited to the illustrated ones. For example, external stimulus applying surfaces 101d2 and external stimulus applying surface 101d3 may be each a concave surface shaped to follow external stimulus applied surface 209 or a convex surface projecting toward external stimulus applied surface 209.

In this example, the other surfaces (namely, surfaces on the opposite side to external stimulus applying surface 101d2 and external stimulus applying surface 101d3) of second housing element 1012d and third housing element 1013d are flat surfaces. The shape of the other surfaces of second housing element 1012d and third housing element 1013d is not limited to the illustrated one.

First housing element 1011d and second housing element 1012d are connected by first joint section 1014d that enables first housing element 1011d and second housing element 1012d to be swingable relative to each other.

First housing element 1011d and third housing element 1013d are connected by second joint section 1015d that enables first housing element 1011d and third housing element 1013d to be swingable relative to each other.

An eccentric motor (not illustrated) is installed in each of first housing element 1011d, second housing element 1012d, and third housing element 1013d.

In this example, since second housing element 1012d and third housing element 1013d are supported swingably relative to first housing element 1011d, the shape of external stimulation section 101D can be adjusted in conformity with the shape of external stimulus applied surface 209.

<Fifth Example of External Stimulation Section>

Figure 3E:
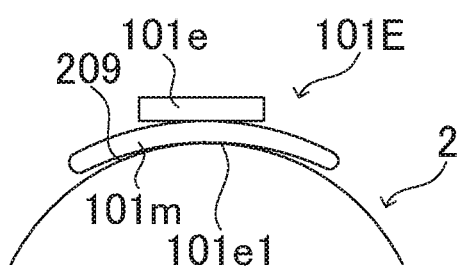
FIG. 3E is a schematic view illustrating a fifth example of the external stimulation section.

FIG. 3E is a schematic view illustrating a fifth example of the external stimulation section. External stimulation section 101E illustrated in FIG. 3E includes housing 101e and external stimulus transmission member 101m.

One surface and the other surface of housing 101e are flat surfaces. The shape of housing 101e is not limited to the illustrated one. An eccentric motor (not illustrated) is installed in housing element 101e.

External stimulus transmission member 101m is arranged between housing 101e and external stimulus applied surface 209 of user 2, and it transmits the external stimulus from housing 101e to external stimulus applied surface 209. External stimulus transmission member 101m has a shape to follow external stimulus applied surface 209.

External stimulus transmission member 101m has external stimulus applying surface 101e1 in one surface (namely, in a surface positioned to face external stimulus applied surface 209). External stimulus applying surface 101e1 is a concave surface shaped to follow external stimulus applied surface 209. The shape of external stimulus applying surface 101e1 is not limited to the illustrated one. The size, the curvature, and so on of external stimulus applying surface 101e1 may be determined as appropriate in conformity with the shape of external stimulus applied surface 209.

The other surface (namely, a surface on the opposite side to external stimulus applying surface 101e1) of external stimulus transmission member 101m is a convex surface having the same curvature as that of external stimulus applying surface 101e1. Housing 101e is fixed to the other surface of external stimulus transmission member 101m. A method of fixing housing 101e and external stimulus transmission member 101m to each other is not limited to particular one. Housing 101e and external stimulus transmission member 101m may be fixed by suitable one of various methods such as fitting, screwing, and attaching with buttons. Alternatively, housing 101e and external stimulus transmission member 101m may not need to be fixed if the external stimulus can be transmitted from housing 101e to external stimulus transmission member 101m in the state in which housing 101e and external stimulus transmission member 101m are held on wearing section 108 (see FIG. 2).

External stimulus transmission member 101m may be disposed in wearing section 108. For example, external stimulus transmission member 101m illustrated in FIG. 3E may be disposed in a holding portion (for example, a pocket) of wearing section 108 in which housing 101e is to be held. In this case, external stimulus applying surface 101e1 is disposed in an inner surface (surface positioned to face external stimulus applied surface 209) of the holding portion of wearing section 108.

In this example, since a large area of external stimulus applying surface 101e1 can be obtained, contact pressure in external stimulus applying surface 101e1 can be reduced. Therefore, user 2 can comfortably use the external stimulus application apparatus without feeling odd.

<Sixth Example of External Stimulation Section>

Figure 3F:
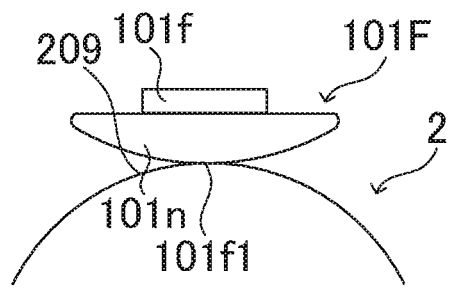
FIG. 3F is a schematic view illustrating a sixth example of the external stimulation section.

FIG. 3F is a schematic view illustrating a sixth example of the external stimulation section. External stimulation section 101F illustrated in FIG. 3F includes housing 101f and external stimulus transmission member 101n. An eccentric motor (not illustrated) is installed in housing 101f.

Housing 101f is similar to that described above in the fifth example.

External stimulus transmission member 101n is arranged between housing 101f and external stimulus applied surface 209 of user 2, and it transmits the external stimulus from housing 101f to external stimulus applied surface 209.

External stimulus transmission member 101n has external stimulus applying surface 101f1 in one surface (namely, in a surface positioned to face external stimulus applied surface 209). External stimulus applying surface 101f1 is a convex surface projecting toward external stimulus applied surface 209. The shape of external stimulus applying surface 101f1 is not limited to the illustrated one. The size, the curvature, and so on of external stimulus applying surface 101f1 may be determined as appropriate in conformity with the shape of external stimulus applied surface 209.

The other surface (namely, a surface on the opposite side to external stimulus applying surface 101f1) of external stimulus transmission member 101n is a flat surface. The shape of the other surface of external stimulus transmission member 101n is not limited to the one illustrated in this example.

In this example, since external stimulus applying surface 101f1 is the convex surface, the external stimulus can be accurately applied to the target area.

<Seventh Example of External Stimulation Section>

Figure 3G:
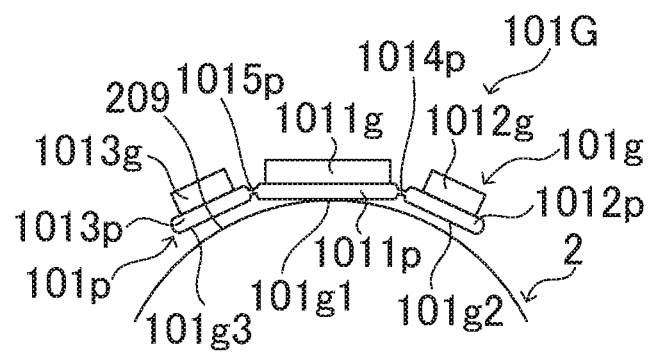
FIG. 3G is a schematic view illustrating a seventh example of the external stimulation section.

FIG. 3G is a schematic view illustrating a seventh example of the external stimulation section. External stimulation section 101G illustrated in FIG. 3G includes housing 101g and external stimulus transmission member 101p.

Housing 101g includes first housing element 1011g, second housing element 1012g, and third housing element 1013g.

First housing element 1011g, second housing element 1012g, and third housing element 1013g have a substantially rectangular box-like shape. One surface and the other surface of each of first housing element 1011g, second housing element 1012g, and third housing element 1013g are flat surfaces.

An eccentric motor (not illustrated) is installed in each of first housing element 1011g, second housing element 1012g, and third housing element 1013g. The shape of first housing element 1011g, second housing element 1012g, and third housing element 1013g is not limited to the illustrated one.

External stimulus transmission member 101p includes first element 1011p, second element 1012p, and third element 1013p.

First element 1011p is arranged at a center of external stimulus transmission member 101p. First element 1011p has a substantially rectangular plate-like shape. First element 1011p has external stimulus applying surface 101g1 in one surface (surface positioned to face external stimulus applied surface 209). External stimulus applying surface 101g1 is a flat surface. The shape of external stimulus applying surface 101g1 is not limited to the illustrated one. For example, external stimulus applying surface 101g1 may be a concave surface shaped to follow external stimulus applied surface 209 or a convex surface projecting toward external stimulus applied surface 209.

In this example, the other surface (namely, a surface on the opposite side to external stimulus applying surface 101g1) of first element 1011p is a flat surface. First housing element 1011g is fixed to the other surface of the first element 1011p. The shape of the other surface of external stimulus applying surface 101g1 is also not limited to the illustrated one.

Second element 1012p and third element 1013p have a substantially rectangular box-like shape. Second element 1012p and third element 1013p are arranged with first element 1011p sandwiched between them.

Second element 1012p and third element 1013p have respectively external stimulus applying surfaces 101g2 and 101g3 in one surfaces (surfaces positioned to face external stimulus applied surface 209). External stimulus applying surface 101g2 and external stimulus applying surface 101g3 are flat surfaces. The shape of external stimulus applying surfaces 101g2 and external stimulus applying surface 101g3 is not limited to the illustrated one. For example, external stimulus applying surfaces 101g2 and external stimulus applying surface 101g3 may be each a concave surface shaped to follow external stimulus applied surface 209 or a convex surface projecting toward external stimulus applied surface 209.

In this example, the other surfaces (namely, surfaces on the opposite side to external stimulus applying surface 101g2 and external stimulus applying surface 101g3) of second element 1012p and third element 1013p are flat surfaces. Second housing element 1012g and third housing element 1013g are fixed respectively to the other surfaces of second element 1012p and third element 1013p. The shape of the other surfaces of external stimulus applying surfaces 101g2 and external stimulus applying surface 101g3 is not limited to the illustrated one.

First element 1011p and second element 1012p are connected by first joint section 1014p that enables first element 1011p and second element 1012p to be swingable relative to each other.

First element 1011p and third element 1013p are connected by second joint section 1015p that enables first element 1011p and third element 1013p to be swingable relative to each other.

In this example, since second element 1012p and third element 1013p are supported swingably relative to first element 1011p, the shape of external stimulation section 101G can be adjusted in conformity with the shape of external stimulus applied surface 209.

<External Stimulus Applying Surface>

External stimulation section 101 has the external stimulus applying surface that is positioned to face the external stimulus applied surface in use. The external stimulus applying surface may be formed by a surface of part of external stimulation section 101.

FIGS. 4A to 4D and FIGS. 5A to 5E illustrate several examples of external stimulus applying surface 101a1. Configurations of external stimulus applying surface 101a1, illustrated in FIGS. 4A to 4D and FIGS. 5A to 5E, can be applied to above-described external stimulation section 101 and 101A to 101G.

<First Example of External Stimulus Applying Surface>

Figure 4A:
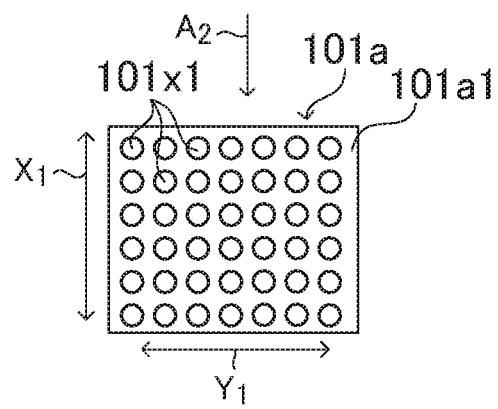
FIG. 4A illustrates a first example of an external stimulus applying surface when viewed in the direction of an arrow $A_1$ in FIG. 3A.
Figure 4B:
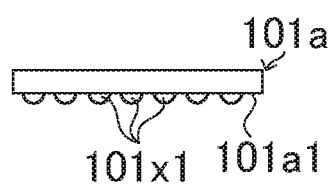
FIG. 4B is an illustration viewed in the direction of an arrow $A_2$ in FIG. 4A.

FIG. 4A is an illustration viewed in the direction of an arrow $A_1$ in FIG. 3A. FIG. 4B is an illustration viewed in the direction of an arrow $A_2$ in FIG. 4A.

Figure 4C:
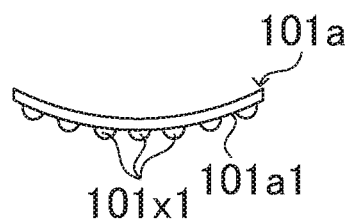
FIG. 4C illustrates Modification 1 of the first example of the external stimulus applying surface when viewed in the direction of the arrow $A_2$ in FIG. 4A.
Figure 4D:
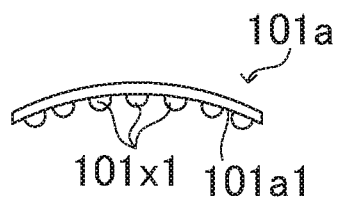
FIG. 4D illustrates Modification 2 of the first example of the external stimulus applying surface when viewed in the direction of the arrow $A_2$ in FIG. 4A.

External stimulus applying surface 101a1 of housing 101a has a rectangular shape in the state illustrated in FIG. 4A. External stimulus applying surface 101a1 includes a plurality of projections 101x1. In this example, projections 101x1 are arrayed at equal intervals in the first direction (direction denoted by an arrow $X_1$ in FIG. 4A) and in the second direction (direction denoted by an arrow $Y_1$ in FIG. 4A) perpendicular to the first direction. Housing 101a may be curved as in Modification 1 and Modification 2 that are illustrated in FIG. 4C and FIG. 4D, respectively.

<Second Example of External Stimulus Applying Surface>

Figure 5A:
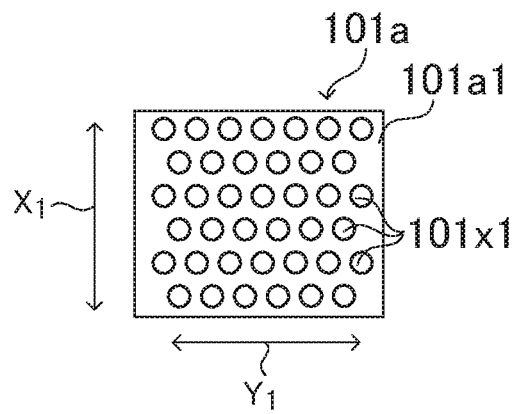
FIG. 5A illustrates a second example of the external stimulus applying surface when viewed in the direction of the arrow $A_1$ in FIG. 3A.

A second example of the external stimulus applying surface will be described below with reference to FIG. 5A. FIG. 5A corresponds to FIG. 4A. In external stimulus applying surface 101a1 illustrated in FIG. 5A, projections 101x1 are arranged in a staggered pattern over the entirety of external stimulus applying surface 101a1.

<Third Example of External Stimulus Applying Surface>

Figure 5B:
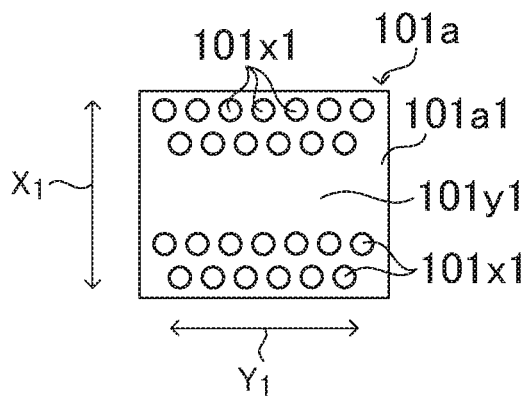
FIG. 5B illustrates a third example of the external stimulus applying surface when viewed in the direction of the arrow $A_1$ in FIG. 3A.

A third example of the external stimulus applying surface will be described below with reference to FIG. 5B. FIG. 5B corresponds to FIG. 4A. Also in external stimulus applying surface 101a1 illustrated in FIG. 5B, projections 101x1 are arranged in a staggered pattern. However, external stimulus applying surface 101a1 illustrated in FIG. 5B has flat surface region 101y1 in which projections 101x1 are not formed, the flat surface region 101y1 spanning over a predetermined range including a central region in the first direction (up-down direction denoted by an arrow $X_1$ in FIG. 5B) (namely, over a range of about ⅓ of the overall length in the first direction).

<Fourth Example of External Stimulus Applying Surface>

Figure 5C:
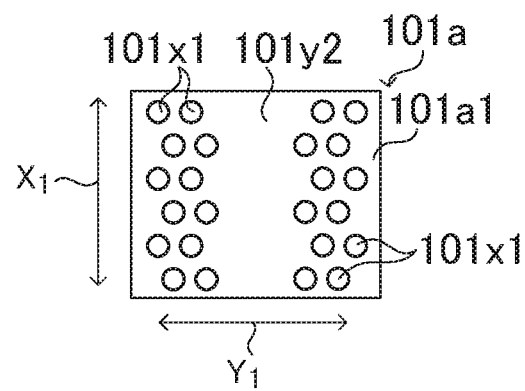
FIG. 5C illustrates a fourth example of the external stimulus applying surface when viewed in the direction of the arrow $A_1$ in FIG. 3A.

A fourth example of the external stimulus applying surface will be described below with reference to FIG. 5C. FIG. 5C corresponds to FIG. 4A. Also in external stimulus applying surface 101a1 illustrated in FIG. 5C, projections 101x1 are arranged in a staggered pattern. However, external stimulus applying surface 101a1 illustrated in FIG. 5C has flat surface region 101y2 in which projections 101x1 are not formed, the flat surface region 101y2 spanning over a predetermined range including a central region in the second direction (direction denoted by an arrow $Y_1$ in FIG. 5C) (namely, over a range of about ⅓ of the overall length in the second direction).

<Fifth Example of External Stimulus Applying Surface>

Figure 5D:
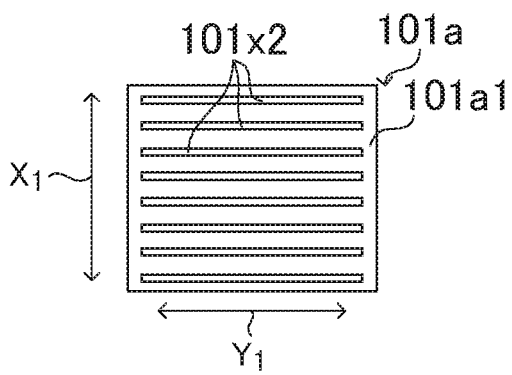
FIG. 5D illustrates a fifth example of the external stimulus applying surface when viewed in the direction of the arrow $A_1$ in FIG. 3A.

A fifth example of the external stimulus applying surface will be described below with reference to FIG. 5D. FIG. 5D corresponds to FIG. 4A. In external stimulus applying surface 101a1 illustrated in FIG. 5D, projections 101x2 are ribs extending in the second direction (direction denoted by an arrow $Y_1$ in FIG. 5D). Projections 101x2 are arrayed at equal intervals in the first direction (direction denoted by an arrow $X_1$ in FIG. 5D). In such a configuration, preferably, the first direction is set to be aligned with a direction in which external stimulus applying surface 101a1 tends to easily slip off relative to external stimulus applied surface 209 (for example, with the vertical direction in use).

<Sixth Example of External Stimulus Applying Surface>

Figure 5E:
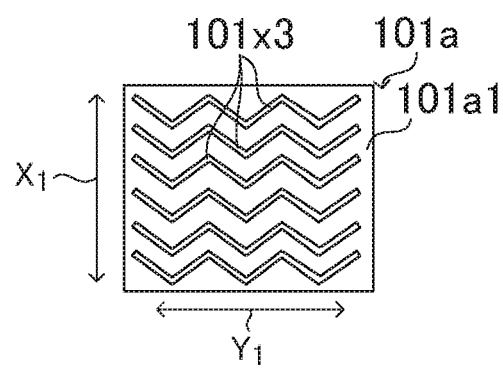
FIG. 5E illustrates a sixth example of the external stimulus applying surface when viewed in the direction of the arrow $A_1$ in FIG. 3A.

A sixth example of the external stimulus applying surface will be described below with reference to FIG. 5E. FIG. 5E corresponds to FIG. 4A. In external stimulus applying surface 101a1 illustrated in FIG. 5E, projections 101x3 are ribs arranged in a zigzag (or Z-folded) pattern and extending in the second direction (direction denoted by an arrow $Y_1$ in FIG. 5E). Projections 101x3 are arrayed at equal intervals in the first direction (direction denoted by an arrow $X_1$ in FIG. 5E). Also in such a configuration, preferably, the first direction is set to be aligned with the direction in which external stimulus applying surface 101a1 tends to easily slip off from external stimulus applied surface 209 (for example, with the vertical direction in use). The shapes of the projections formed on the external stimulus applying surface are not limited to those ones illustrated in the above-described first to sixth examples.

The above-described structures in which external stimulus applying surface 101a1 has the projections can not only realize selective application of the external stimulus to external stimulus applied surface 209, but also improve breathability between external stimulus applying surface 101a1 and external stimulus applied surface 209.

Above-described external stimulation section 101 (that can also be equivalently read as each of other external stimulation sections 101A to 101G) is preferably arranged at a position including a center region of the external stimulus applied surface. The number of external stimulation sections 101 may be singular or plural. When the number of external stimulation sections 101 is plural, external stimulation sections 101 may be arranged in a distributed layout corresponding to the external stimulus applied surface of one target area. In another example, when the number of external stimulation sections 101 is plural, external stimulation sections 101 may be arranged corresponding to the external stimulus applied surfaces of different target areas.

When the number of external stimulation sections 101 is plural, external stimulation sections 101 are preferably arranged at such positions that the external stimuli generated from the external stimulation sections do not weaken each other. Furthermore, when the number of external stimulation sections 101 is plural, external stimulation sections 101 are preferably arranged at such positions that the external stimuli (for example, vibrations) generated from the external stimulation sections strengthen each other.

When the number of external stimulation sections 101 is plural, external stimulation sections 101 are preferably arranged at such positions that the external stimuli (for example, vibrations) generated from the external stimulation sections strengthen each other in the target area. More preferably, external stimulation sections 101 are arranged at such positions that the external stimuli (for example, vibrations) generated from the external stimulation sections strengthen each other in a center zone of the target area. With that configuration, the external stimulus (for example, vibration) applied to the target area can be amplified while the stimulus applied to the external stimulus applied surface (namely, the skin) is kept small.

In addition, external stimulation sections 101 are preferably arranged at such positions that the external stimuli (for example, vibrations) generated from the external stimulation sections strengthen each other in the center zone of the target area.

External stimulation section 101 may be held on wearing section 108 in the state adjustable in its position. External stimulation section 101 may be removable from wearing section 108.

External stimulation section 101 may not need to be held on wearing section 108 on condition that it is connected to control section 103. The connection between external stimulation section 101 and control section 103 may be wired or wireless.

External stimulation section 101 has the external stimulus applying surface that is positioned to face the external stimulus applied surface in use. The external stimulus applying surface may be formed by a surface of part of external stimulation section 101. Alternatively, the external stimulus applying surface may be formed by a surface of another member fixed to external stimulation section 101. In this case, the other member is a member capable of transmitting the external stimulus generated from external stimulation section 101 to the external stimulus applied surface.

The external stimulus applying surface may be a curved surface. In this case, the external stimulus applying surface may be a curved surface projecting toward the external stimulus applied surface. With such a configuration, the external stimulus is more easily transmittable to user 2 in use. In addition, such a configuration is effective in reducing an uncomfortable feeling of user 2 in use.

Alternatively, the external stimulus applying surface may be a curved surface shaped to follow the external stimulus applied surface. By using that external stimulus applying surface, a contact area between the external stimulus applying surface and the external stimulus applied surface is increased. Moreover, the external stimulus is transmitted from external stimulation section 101 to the external stimulus applied surface in multiple ways.

External stimulus applying surface may be a flat surface or a concave-convex surface including concave portions and convex portions. Regardless of the external stimulus applying surface having which one of the above-mentioned shapes, it is preferable that an outer peripheral edge of the external stimulus applying surface does not include any pointed portion (namely, any angled portion). Such a configuration is effective in reducing an uncomfortable feeling of user 2 in use.

Above-described external stimulation section 101 is a vibrator and includes, for example, a housing (see FIGS. 3A to 3G) and an eccentric motor (not illustrated).

The housing includes, for example, an accommodation space and the above-described external stimulus applying surface formed in part of an outer surface of the housing. More specifically, the housing is a rectangular parallelepiped box-like member. The housing may be a disk-shaped box-like member. The housing may have the above-described external stimulus applying surface. When the housing has the external stimulus applying surface, the external stimulus applying surface may be fixed to the housing in a replaceable manner.

The housing material is preferably, for example, a material that does not absorb vibration generated by the eccentric motor. Furthermore, the housing material is preferably a material that is hard to convert vibration energy to thermal energy and to dissipate the thermal energy.

That type of housing material is, for example, synthetic resin. More specifically, the housing material is, for example, synthetic resin such as polyolefins including an acrylonitrile-butadiene-styrene (ABS) copolymer, polyethylene (PE), and polypropylene (PP).

The housing material is not limited to the above-mentioned materials. The housing material may be, for example, metal. When the housing is brought into direct contact with the skin of the user, a metal having high affinity with the living body is preferably used as the metal material. When the housing is not brought into direct contact with the skin of the user, various metal materials (such as iron-based alloys and aluminum alloys) except for titanium may be optionally used as the metal material.

The eccentric motor is constituted by, for example, a DC motor and a weight having the eccentric center of gravity. The weight is fixed to a rotation axis of the DC motor. An operation of the DC motor is controlled by control section 103 described later. Various types of vibrators known so far may be optionally used in external stimulation section 101.

The size of external stimulation section 101 (specifically, of the housing) is not limited to particular one. The size of external stimulation section 101 is preferably set so as not to impede the motion of user 2. The size of external stimulation section 101 is determined as appropriate depending on the size of the target area (namely, the area of the external stimulus applied surface).

When the external stimulus is the electrical stimulus, the electrode section includes an electrode base material (not illustrated) that is formed by weaving a metallic thread, and a gel-like adhesive layer that is disposed on a surface of the electrode base material and that can conduct electric power therethrough. The electrode section is not limited to the above-mentioned structure and may have any suitable structure enabling the electrical stimulus to be applied to muscles.

When the target area is the vastus medialis muscle of user 2, external stimulation section 101 has a rectangular parallelepiped shape with a length of 40 mm, a width of 60 mm, and a height of 30 mm, for example. In this case, external stimulation section 101 has the external stimulus applying surface in its surface on the side coming into contact with user 2 in use.

The target area in the body of user 2 will be described below. Examples of the target area in the body of user 2 are chest muscles, abdominal muscles, back muscles, shoulder muscles, arm muscles, leg muscles, and buttock muscles of user.

The chest muscles include, for example, pectoralis major. The abdominal muscles include, for example, rectus abdominis muscle, abdominal external oblique muscle, abdominal internal oblique muscle, and iliopsoas muscle. The back muscles include, for example, erector spinae, latissimus dorsi muscle, teres major muscle, teres minor muscle, and infraspinatus muscle. The shoulder muscles include, for example, deltoid muscle and trapezius.

The arm muscles include, for example, biceps brachii muscle and triceps brachii muscle. The leg muscles include, for example, quadriceps femoris muscles (rectus femoris muscle, vastus intermedius muscle, vastus medialis muscle, and vastus lateralis muscle), and hamstring (including biceps femoris muscle, semitendinosus muscle, and semimembranosus muscle). The buttock muscles include, for example, gluteus minimus muscle, gluteus medius muscle, and gluteus maximus muscle.

<Detection Section>

Detection section 102 detects changes in the body of user 2 during the motion of user 2. Detection section 102 detects, as a physical quantity (change value), change in an area (for example, a knee) that is changed corresponding to the target area (for example, vastus medialis muscle 203, see FIG. 2) during the motion of user 2. Then, detection section 102 sends the detected physical quantity to control section 103 described later. Detection section 102 detects the physical quantity at predetermined intervals and sends the detected physical quantity to control section 103.

The above-mentioned physical quantity includes, for example, a displacement, a time, an angle, an angular speed, a speed, an acceleration, a current, a voltage (for example, a myoelectric potential), and a pressure. Those physical quantities are detected by sensors adapted for the physical quantities to be detected. The value detected by detection section 102 is given as information (hereinafter referred to as "first information during the motion") that is used in control section 103 to determine the timing of controlling external stimulation section 101 (namely, the timing of switching ON/OFF the vibration of external stimulation section 101).

During the motion of user 2, detection section 102 may further detect information (hereinafter referred to as "second information during the motion") regarding user 2 except for the first information during the motion. The second information during the motion includes, for example, information regarding a body temperature, a blood pressure, a heartrate, a fat mass, and a muscle mass during the motion of user 2. The second information during the motion further includes information corresponding to the motion of user 2 (namely, the type of exercise). When the motion of user 2 is walking (including running), the information regarding the motion includes, for example, the number of steps, a step length, a walking cycle, a walking speed, an acceleration (namely, a change rate of the walking speed), an extension angle of the knee, an adduction angle (twist angle) of the knee, and strengths of the leg muscles. The second information may further include a wearing time during which user 2 keeps wearing external stimulus application apparatus 10. The first information during the motion and the second information during the motion may be used in common in some cases. For example, the angle, the angular speed, the speed, the acceleration, the voltage, and so on that have been mentioned as examples of the first information during the motion can be each used as an index (such as a bending (angle) of the knee or a walking speed) when the effect of rehabilitation is measured. Moreover, when one knee is injured, the step length, the walking cycle, the acceleration, the extension angle, and so on are often different between left and right legs due to the injury. Therefore, detection section 102 may be attached to each of the left and right legs.

Detection section 102 may detect, as the second information, a bending or extending angle of a joint (namely, a full range of motion (FROM) of a joint), such as a knee joint, under control of control section 103 or in accordance with the operation by user 2. The detection by detection section 102 may be performed, for example, once a day or once before and after rehabilitation. The detection by detection section 102 is performed in a period during which detection section 102 is operated, but the first information is not detected.

Detection section 102 may detect, as the second information, the muscle strength in the target area (for example, the vastus medialis muscle) of user 2 under control of control section 103 or in accordance with the operation by user 2. The detection by detection section 102 may be performed, for example, once a day or once before and after rehabilitation. The detection by detection section 102 is performed in a period during which detection section 102 is operated, but the first information is not detected.

Detection section 102 may detect information (hereinafter referred to as "third information during the motion") regarding the surroundings of user 2 during the motion of user 2. The third information during the motion includes, for example, an air temperature, a humidity, an atmospheric pressure, an altitude, and location information (GPS: Global Positioning System).

Examples of detection section 102 are sensors such as an angle sensor, an angular speed sensor, an acceleration sensor, and a myoelectric potential sensor. Detection section 102 is not limited to those sensors.

Detection section 102 may include sensors that detect the second information during the motion. Those sensors are, for example, a body temperature sensor, a blood pressure sensor, a heartrate sensor, and a step sensor. Detection section 102 may further include sensors that detect the third information during the motion. Those sensors are, for example, an air temperature sensor, an atmospheric pressure sensor, and a GPS sensor.

The timing of detecting the first information, the second information, or the third information during the motion by the above-mentioned various sensors can be optionally set depending on the purpose in consideration of timings of various motions in the walking, such as the timing of landing, the timing of full extension of the knee, the timing of liftoff of the foot from the ground, the timing at the middle of a time from landing to liftoff, and the timing after 0.1 sec from landing. Furthermore, regarding exercise such as running and waking up and down stairs, the timings of detecting various kinds of information may be set to similar timings to those set for the above-described motions in the walking.

Regarding the various kinds of information thus detected or obtained, detection section 102 may send and store, for example, all data to and in later-described server 11. Alternatively, detection section 102 may send and store average values of data in an optionally set period to and in later-described server 11.

Detection section 102 may send and store data per unit time, for example, per minute or hour, to and in the server. Regarding the data thus obtained, all or part of the data is stored in a storage section inside external stimulus application apparatus 10 or an external storage apparatus (such as a server).

In the case of verifying the effect of rehabilitation, the measurement frequency of, for example, the fat mass or the muscle mass may be set to be low. In the case of verifying the effect of rehabilitation, the measurement frequency of changes in the acceleration and the angle is preferably set to be high such as per minute, for example. Also in the case of processing data to average values and storing the average values, the data may be obtained and stored per minute, per hour, or per day, for example, depending on the purpose of use of the data.

After verification on the effect of rehabilitation or treatment, the data thus obtained can be used as, for example, an index for determining hospital visit for the rehabilitation, an index for determining hospital visit for medical care or clinical examination by a doctor, an index for medication, or an index for indicating the effect of muscle training in sports. In addition, the obtained data can be further used as an index for adjusting, fabricating, or selecting fittings such as an insole and a joint supporter.

Detection section 102 is connected to control section 103. The connection between detection section 102 and control section 103 may be wired or wireless. In this embodiment, detection section 102 is held on wearing section 108 described later.

Detection section 102 is arranged in an area (hereinafter referred to as a "detected area") of the body of user 2, the detected area being changed corresponding to the target area during the motion of user 2. The detected area may be the same as or different from the target area in the body of user 2.

When the value detected by detection section 102 is affected by the external stimulus (for example, vibration) generated from external stimulation section 101 in the body-worn state, detection section 102 is preferably arranged at a position where it is less affected. For example, when the target area is vastus medialis muscle 203 (see FIG. 2), detection section 102 is preferably arranged at a position away from at least 90 degrees to 180 degrees, preferably 120 degrees to 180 degrees, from the vastus medialis muscle in the direction along an outer periphery of the knee of user 2.

When the target area is the muscle in a femoral region of user 2 (for example, the vastus medialis muscle or the vastus lateralis muscle), detection section 102 may be arranged in a lower leg region of user 2. Detection section 102 is preferably arranged at a position which is changed (namely, actively moved) in accordance with the motion of the target area and at which detection section 102 is less affected by the external stimulus (for example, vibration) generated from external stimulation section 101.

As an example regarding the layout of the target area and detection section 102, when the target area is the lower leg region of user 2, detection section 102 is preferably arranged in the femoral region of user 2. When the target area is the muscle in an upper arm region of user 2, detection section 102 is preferably arranged in a forearm region of user 2. When the target area is the back muscle of user 2, detection section 102 is preferably arranged in the femoral region of user 2. When the target area is the buttock muscle of user 2, detection section 102 is preferably arranged in the femoral region of user 2. When the target area is the shoulder muscle of user 2, detection section 102 is preferably arranged in the upper arm region of user 2.

Detection section 102 may be covered with an anti-vibration member having anti-vibration properties. The above-described features are effective in reducing false detection by detection section 102.

For example, when the detected area is the joint of user 2, detection section 102 detects displacement amounts of the joint caused by extension, bending, rotation, and so on of the joint.

Figure 2:
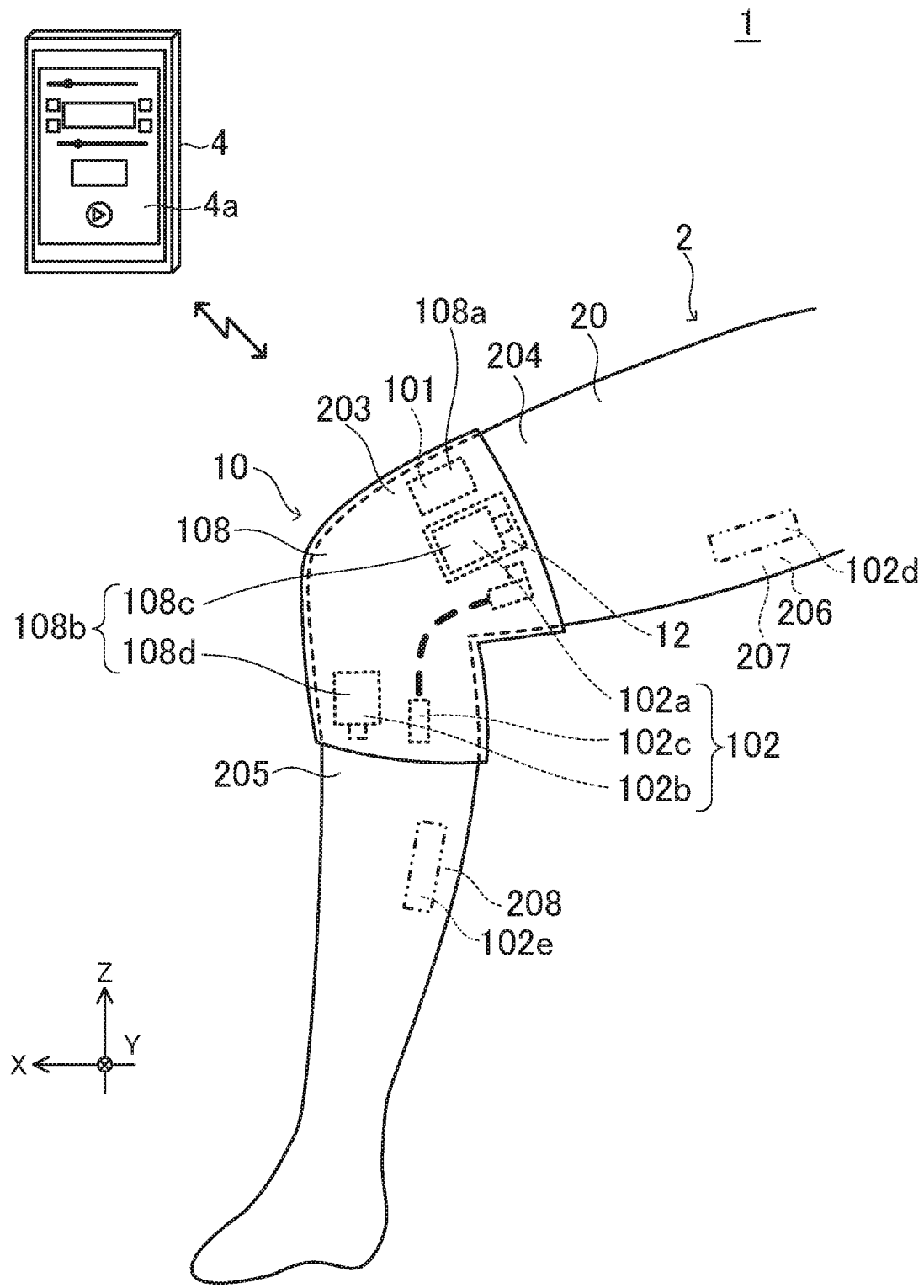
FIG. 2 illustrates a state in which a user wears the external stimulus application apparatus.

FIG. 2 illustrates external stimulus application apparatus 10 when the detected area is the knee of user 2 and the target area is vastus medialis muscle 203 in the leg of user 2. The expression "the knee of user 2" may include the knee joint and areas around the knee joint (namely, part of the femoral region or the lower leg region).

In external stimulus application apparatus 10 described above, detection section 102 includes first sensor 102a and second sensor 102b. First sensor 102a is, for example, an acceleration sensor and is arranged in femoral region 204 of user 2 in the body-worn state. When the external stimulus is the vibratory stimulus, first sensor 102a is preferably held on wearing section 108 in the state covered with anti-vibration member 12.

The reason why anti-vibration member 12 is disposed is that external stimulation section 101 and first sensor 102a are both arranged in femoral region 204. When the external stimulus is the vibratory stimulus, anti-vibration member 12 makes the vibration of external stimulation section 101 less transmitted to first sensor 102a. Such a configuration is effective in improving the detection accuracy of first sensor 102a. Anti-vibration member 12 may be omitted.

Second sensor 102b is an acceleration sensor and is arranged in lower leg region 205 of user 2 in the body-worn state. In this embodiment, second sensor 102b is not covered with the anti-vibration member. The reason is that, while external stimulation section 101 is arranged in femoral region 204, second sensor 102b is arranged in lower leg region 205. Second sensor 102b may be held on wearing section 108 in the state covered with the anti-vibration member.

During the motion of user 2, first sensor 102a and second sensor 102b detect accelerations in the predetermined directions in femoral region 204 and lower leg region 205, respectively. The predetermined directions are, for example, three directions orthogonal to one another, namely the X direction, the Y direction, and the Z direction (see FIG. 2).

The X direction corresponds to the back-forth direction of user 2 (left-right direction in FIG. 2). The Y direction corresponds to the left-right direction of user 2 (direction perpendicular to the drawing sheet of FIG. 2). The Z direction corresponds to the vertical direction (up-down direction in FIG. 2). One side (for example, the front side, the right side, or the upper side) in each of the above-mentioned directions is assumed to be a positive direction. The other side (for example, the rear side, the left side, or the lower side) in each of the above-mentioned directions is assumed to be a negative direction. Leg 20 of user 2 illustrated in FIG. 2 is the right leg of user 2.

Detection section 102 may include, in addition to first sensor 102*a* and second sensor 102*b*, third sensor 102*c* that is, for example, an angle sensor. When the detected area is the knee of user 2, third sensor 102*c* is arranged over a range spanning from femoral region 204 to lower leg region 205 of user 2. Third sensor 102*c* detects the angle of the knee joint of user 2 (namely, the angle formed between femoral region 204 and lower leg region 205) during the motion of user 2.

When the detected area is the elbow joint of user 2, first sensor 102*a* is arranged in the upper arm region of user 2 and second sensor 102*b* is arranged in the forearm region of user 2 in the body-worn state. In this case, detection section 102 may include, in addition to first sensor 102*a* and second sensor 102*b*, third sensor 102*c* that is, for example, an angle sensor.

When the detected area is the elbow joint of user 2, third sensor 102*c* is arranged over a range spanning from the upper arm region to the forearm region of user 2. When the detected area is the elbow joint of user 2, the target area is the arm muscle of user 2.

<Control Section>

Control section 103 (see FIG. 1) includes a CPU (Central Processing Unit), a ROM (Read Only Memory), a RAM (Random Access Memory), an input port, an output port, and so on.

Control section 103 can turn ON/OFF the external stimulus (for example, vibration) from external stimulation section 101 in accordance with a specific condition. More specifically, when the external stimulus is the vibratory stimulus, control section 103 vibrates external stimulation section 101 under a predetermined vibration condition when the detected value (physical quantity), which has been received from detection section 102, satisfies a predetermined condition. In more detail, control section 103 compares the detected value (physical quantity), which has been received from detection section 102, with a predetermined threshold, and vibrates external stimulation section 101 under the predetermined vibration condition when the comparison result satisfies a vibration start condition (namely, a predetermined condition).

When the external stimulus application apparatus includes an electrical stimulation section (not illustrated) instead of vibration stimulation section 101, control section 103 can turn ON/OFF output of a current from the electrical stimulation section in accordance with a specific condition. In this case, control section 103 controls output of a pulse current supplied from a power supply section (not illustrated) to a pulse generation section (electrode section, not illustrated). Display section 4*a* displays information indicating, for example, the muscle to which the electrical stimulus is applied, the intensity of the electrical stimulus, and pulse characteristics (such as a frequency, an amplitude, a waveform, and a stimulus application pattern). Control section 103 and display section 4*a* receive electric power supplied from the power supply section. A program for controlling an output mode of the current from the electrode section is stored in storage section 105. The pulse generation section (electrode section) outputs a low-frequency signal of 2 Hz to 100 Hz, preferably 2 to 40 Hz, to the control section. Turning ON/OFF of the power supply by the control section may be performed by a switch in an operating section. The operating section may include switches and dials for making various kinds of settings. A plurality of electrical stimulation modes can be optionally selected by operation made on the operating section.

For example, when the value detected by detection section 102 is equal to or greater than the predetermined threshold, control section 103 determines that an external stimulation start condition is satisfied. On the other hand, when the value detected by detection section 102 is smaller than the predetermined threshold, control section 103 determines that the external stimulation start condition is not satisfied.

Control section 103 may set a stimulation time (for example, a vibration duration time or a duration time of the current flowing in the electrode) of external stimulation section 101. In this case, control section 103 stops the operation of external stimulation section 101 when the stimulation time has expired.

As the above-mentioned predetermined threshold, a value corresponding to the target area, the detected area, and the type of the physical quantity to be detected by detection section 102 is stored in, for example, the ROM of control section 103 in advance. Upon receiving the detected value from detection section 102, control section 103 compares the detected value, received from detection section 102, with the predetermined threshold stored in advance.

The predetermined threshold in the case in which the target area is the muscle of user 2 is described. The threshold in this case is a value based on which control section 103 can determine the contracted state of the target area. The contracted state of the target area stands for the state in which a myoelectric potential is generated in the target area.

The predetermined threshold may be a value based on which control section 103 can determine the state before the generation of the myoelectric potential in the target area by a predetermined time.

When the motion (for example, walking or running) of the user is a series of repeated motions in which a predetermined motion is repeated, control section 103 may store the timing at which external stimulus application apparatus 101 has been operated (for example, vibrated) in the preceding predetermined motion in the series of repeated motions. Control section 103 may store the above-mentioned timing in storage section 105. Control section 103 may determine, based on the above-mentioned timing, the timing of operating external stimulation section 101.

The predetermined threshold in the walking motion is described. Control section 103 specifies, from changes in the value detected by the acceleration sensor during the walking, the timing at which the foot of user 2 comes into contact with the ground, and then sets a threshold for that timing. Based on the set threshold, control section 103 determines the moment of landing, the time point immediately before the landing, and the time point immediately after the landing in the walking motion of user 2.

Preferably, control section 103 specifies, from the preceding cycle of the walking motion, the timing at which the foot of user 2 comes into contact with the ground, and then sets a threshold for that timing. As a result, control section 103 can more accurately determine the moment of landing, the time point immediately before the landing, and the time point immediately after the landing in the walking motion of user 2.

When control section 103 receives the detected values from a plurality of detection sections (for example, an acceleration sensor and an angle sensor), control section 103 may operate (for example, vibrate) external stimulation section 101 if at least one of the detected values satisfies the external stimulation start condition.

From the viewpoint of increasing the accuracy of the timing of applying the external stimulus, when control section 103 receives the detected values from a plurality of detection sections, control section 103 preferably operates (for example, vibrates) external stimulation section 101 only if all of the detected values satisfy the external stimulation start conditions.

Control section 103 compares the detected value, received from detection section 102, with the predetermined threshold, and stops the operation of external stimulation section 101 if the comparison result satisfies an end condition.

When control section 103 performs any of the above-described determinations, a signal attributable to the external stimulus (for example, vibration) generated from external stimulation section 101 may be removed from the detected value received from detection section 102. Such a signal can be removed by, for example, a method of performing a filtering process on the detected value received from detection section 102 by using a filter (for example, a bandpass filter) that removes a predetermined frequency (cutoff frequency).

The frequency of the external stimulus (for example, vibration) generated from external stimulation section 101 is known because it is set by control section 103. Control section 103 may set, as the cutoff frequency of the filter, the same frequency as that of the external stimulus set by external stimulation section 101. In such a case, control section 103 may take into consideration, as a delay time, a time until the external stimulus (for example, vibration) generated from external stimulation section 101 is detected by detection section 102 when the filtering process is executed.

Control section 103 sets an external stimulus condition in external stimulation section 101. When the external stimulus is the vibratory stimulus, the external stimulus condition may include at least one among, for example, a vibration time, an amplitude, a vibration frequency, and a vibration pattern. Control section 103 obtains the external stimulus condition from storage section 105, server 11, or external apparatus 4.

When the external stimulus is the vibratory stimulus, the amplitude in the external stimulus condition (vibration condition) is, for example, 0.05 mm to 5 mm. Preferably, the amplitude is 0.1 mm to 1 mm. The vibration frequency is, for example, 0.5 Hz to 1000 Hz. The vibratory stimulus with the above-described amplitude and vibration frequency can improve the effect of rehabilitation.

When the external stimulus is the electrical stimulus, the frequency in the external stimulus condition (electrical stimulus condition) is, for example, 2 Hz to 100 Hz and preferably 2 Hz to 40 Hz. The electrical stimulus may be a pulse wave or a burst wave including a plurality of divided electrical signals.

As described later, control section 103 receives, from external apparatus 4, information (for example, information regarding the vibration intensity and the vibration mode) that is input from display section 4a of external apparatus 4. Control section 103 sets the information received from external apparatus 4 in external stimulation section 101.

When user information and information regarding the motion of the user are input from input section 106 described later, control section 103 obtains, from storage section 105, the external stimulus condition (for example, the vibration condition) corresponding to the input information. Control section 103 sets the obtained external stimulus condition in external stimulation section 101. The information regarding the motion of the user is, for example, information regarding the type of exercise performed by the user and the strength of the exercise.

Alternatively, control section 103 may obtain, from server 11, the external stimulus condition (for example, the vibration condition) corresponding to the user information and the information regarding the motion of the user, which have been input from input section 106. Thereafter, control section 103 sets the obtained external stimulus condition in external stimulation section 101.

Control section 103 stores, peruser, the user information, the information regarding the motion of the user, and the external stimulus condition for the external stimulus that has been applied to the target area of the user by external stimulation section 101, and sends them to storage section 105.

Figures 9A, 9B:
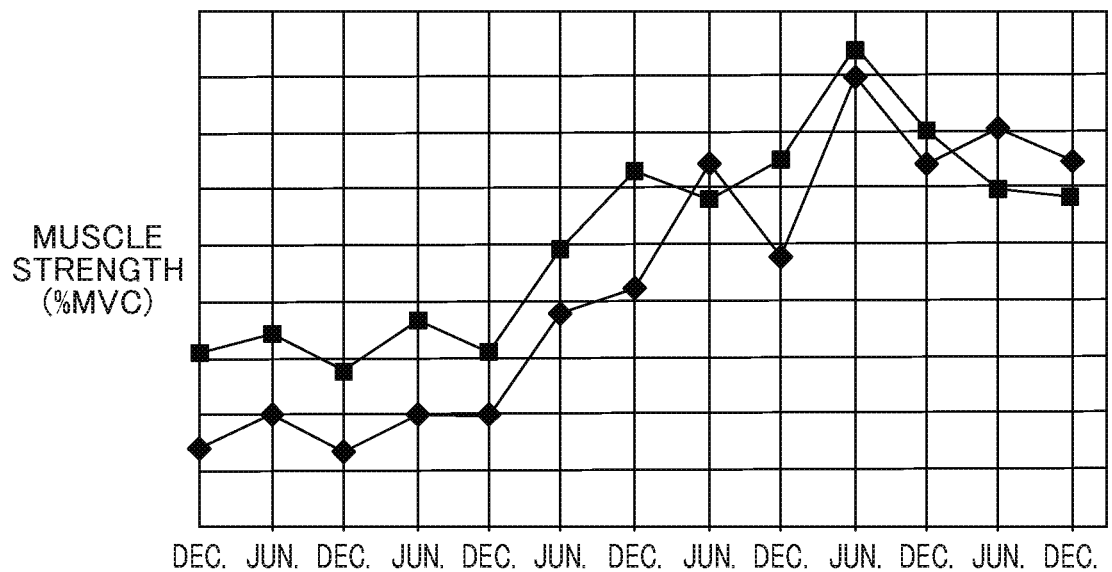
FIG. 9A illustrates an example of a chart produced from graphic data.
FIG. 9B illustrates an example of a table produced from graphic data.

In accordance with the information (for example, the second information during the motion) received from detection section 102, control section 103 may produce graphic data (see FIGS. 9A and 9B) to check, for example, the effect of rehabilitation and the effect of treatment. Control section 103 may send the produced graphic data to external apparatus 4. External apparatus 4 may display the received graphic data on display section 4a. By viewing the graphic data displayed on display section 4a, the user can check the effect of rehabilitation and the state of his or her body during the motion.

Control section 103 may send the information received from detection section 102 to storage section 105. Furthermore, control section 103 may send the information received from detection section 102 to server 11. Server 11 stores the received information in a server-side storage section 11b described later.

When there are multiple external stimulation sections 101, control section 103 executes the above-described control for each of external stimulation sections 101. When there are multiple external stimulation sections 101, control section 103 may operate (for example, vibrate) external stimulation sections 101 at the same timing. When there are multiple external stimulation sections 101, control section 103 may vibrate external stimulation sections 101 at different timings. When external stimulation section 101 is the electrical stimulation section (not illustrated), control section 103 may control the electrical stimulation section to output a current at the same timing as the above-described timing of operating external stimulation section 101. The timing of applying the external stimulus, explained in Operation Examples 1 to 5 described later, may be replaced with the timing of applying the vibratory stimulus and the timing of applying the electrical stimulus (namely, the timing of causing the electrical stimulation section to output the current).

Operation Example 1

Figure 6:
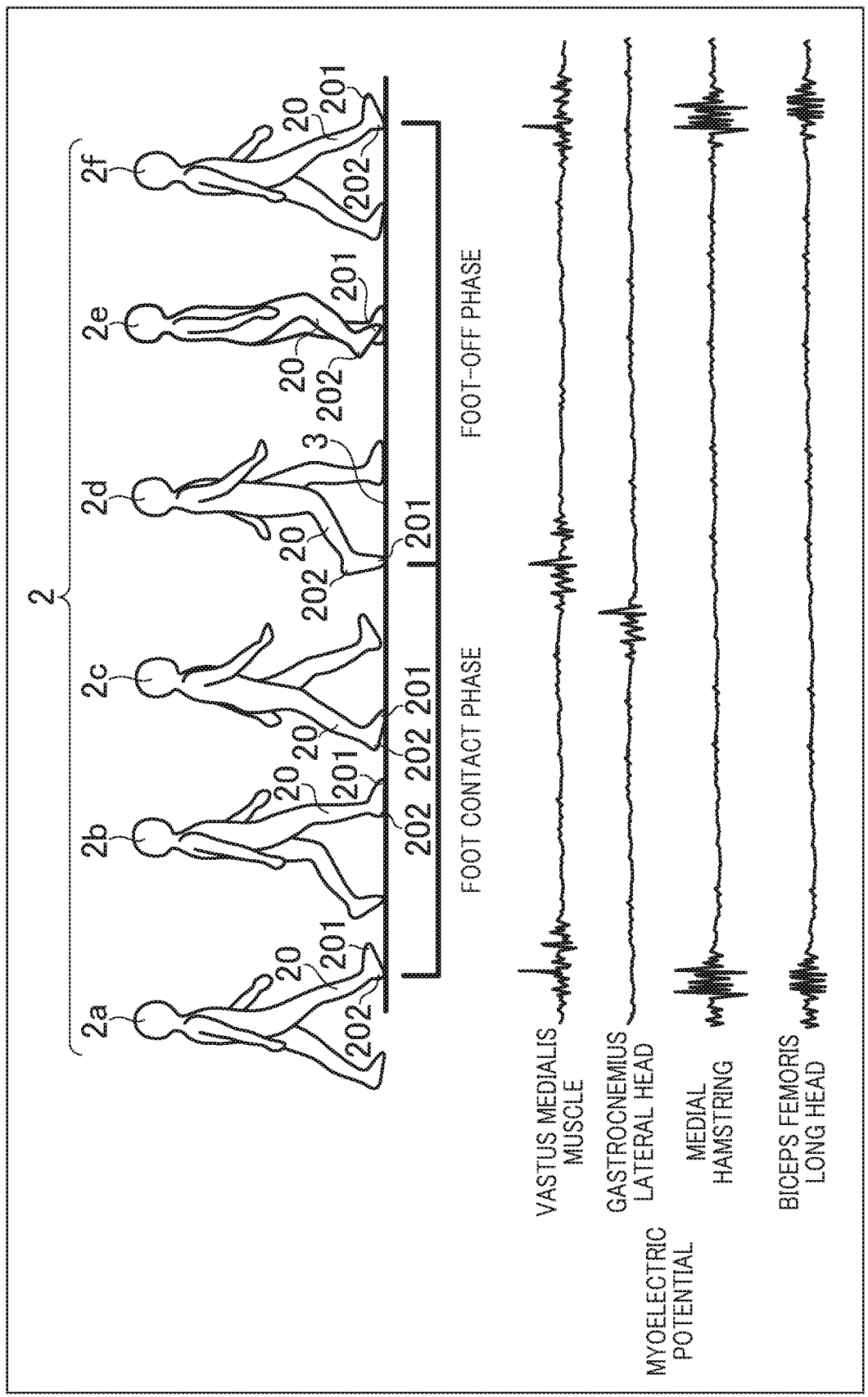
FIG. 6 illustrates relations between a waking motion and myoelectric potentials in various muscles during the walking motion.

Operation Example 1 of control section 103 in which the motion of user 2 is the walking motion, the detected area is the knee of user 2, and the target area is vastus medialis muscle 203 will be described below with reference to FIG. 6. FIG. 6 illustrates the waking motion of user 2 and myoelectric potentials in various muscles (vastus medialis muscle 203, medial hamstring 206, biceps femoris long head 207, and gastrocnemius lateral head 208) of user 2 in accordance with the walking motion.

The walking motion of user 2 consists of afoot contact phase (also called a stance phase) and a foot-off phase (also called a swing phase). One period of the walking stands for a time span from the state in which heel 202 of one leg 20 of user 2 comes into contact with ground 3 (namely, the state of user 2*a*) to the state in which heel 202 of one leg 20 comes into contact with ground 3 again (namely, the state of user 2*f*).

The foot contact phase stands for a time span in one period of the walking motion during which foot 20 of user 2 is in contact with ground 3 (namely, a time span from the state of user 2*a* to the state of user 2*c*). On the other hand, the foot-off phase stands for a time span in one period of the walking motion during which foot 20 of user 2 is apart from ground 3 (namely, a time span from the state of user 2*d* to the state of user 2*f*). In FIG. 6, user 2*a* and user 2*f* are in the same state.

More specifically, a start point of the foot contact phase (hereinafter referred to as a "foot-contact phase start point") is the moment (corresponding to the state of user 2*a*, 2*f*) at which heel 202 of foot 20 of user 2, the heel 202 being apart from ground 3 (namely, being in the foot-off state), comes into contact with ground 3.

On the other hand, an end point of the foot contact phase (hereinafter referred to as a "foot-contact phase end point") is the moment (corresponding to the state of user 2*c*) at which toe 201 of foot 20 of user 2, the toe 201 being in contact with ground 3 (namely, being in the foot contact state), leaves ground 3.

A start point of the foot-off phase (hereinafter referred to as a "foot-off phase start point") is the moment (corresponding to the state of user 2*d*) at which toe 201 of foot 20 of user 2, the toe 201 being in the foot contact state, leaves ground 3.

On the other hand, an end point of the foot-off phase (hereinafter referred to as a "foot-off phase end point") is the moment (corresponding to the state of user 2*f*) at which heel 202 of foot 20 of user 2, the heel 202 being in the foot-off state, comes into contact with ground 3. Thus the foot-contact phase start point overlaps the foot-off phase end point. The foot-contact phase end point overlaps the foot-off phase start point.

As illustrated in FIG. 6, vastus medialis muscle 203 of user 2 generates the myoelectric potential at the foot-contact phase start point (that is also the foot-off phase end point) and the foot-contact phase end point (that is also the foot-off phase start point).

In this embodiment, control section 103 controls external stimulation section 101 such that the external stimulus (for example, the vibratory stimulus or the electrical stimulus) is applied to vastus medialis muscle 203 of user 2 in the foot contact phase of the walking motion.

More specifically, control section 103 compares the detected value (namely, the first information during the motion), received from detection section 102, with the predetermined threshold. Then, control section 103 determines whether the walking motion of user 2 is in the foot contact phase. If the determination result indicates that the walking motion of user 2 is in the foot contact phase, control section 103 operates external stimulation section 101 under the predetermined external stimulus condition. In other words, when the walking motion of user 2 is in the foot contact phase, the above-described external stimulus start condition is satisfied.

Control section 103 may determine whether the walking motion of user 2 is in the state immediately before the foot-contact phase start point (for example, before 0.5 sec). If the determination result indicates that the walking motion of user 2 is in the state immediately before the foot-contact phase start point, control section 103 operates external stimulation section 101 under the predetermined external stimulus condition. In other words, when the walking motion is in the state immediately before the foot-contact phase start point, the above-described external stimulus start condition is satisfied.

With the above-described feature, the external stimulus from external stimulation section 101 is efficiently applied to vastus medialis muscle 203 of user 2 at the foot-contact phase start point at which vastus medialis muscle 203 generates the myoelectric potential.

Control section 103 may determine whether the walking motion of user 2 is in the state immediately before the foot-contact phase end point (for example, before 0.5 sec). If the determination result indicates that the walking motion of user 2 is in the state immediately before the foot-contact phase end point, control section 103 controls external stimulation section 101 to generate the stimulus under the predetermined external stimulus condition. In other words, when the walking motion of user 2 is in the state immediately before the foot-contact phase end point, the above-described external stimulus start condition is satisfied.

With the above-described feature, the external stimulus from external stimulation section 101 is efficiently applied to the target area of user 2 at the foot-contact phase end point at which vastus medialis muscle 203 generates the myoelectric potential.

When the external stimulus start condition is satisfied, control section 103 may operate external stimulation section 101 for a predetermined time. In this case, the predetermined time is preferably set to a span including both the foot-off phase start point and the foot-contact phase end point. The predetermined time may be set to a span including at least one of the foot-off phase start point and the foot-contact phase end point.

Control section 103 may stop the operation of external stimulation section 101 between the foot-off phase start point and the foot-contact phase end point. In this case, the external stimulus at the foot-off phase start point and the external stimulus at the foot-contact phase end point become discontinuous.

For example, when the detected value (physical quantity) detected by detection section 102 is the angle of the knee joint of user 2, the situation that the walking state of user 2 is in the foot contact phase can be detected by setting the predetermined threshold to 180°.

The reason is that, during the walking motion of user 2, the angle of the knee joint takes 180° not only immediately before heel 202 of user 2 comes into contact with the ground (namely, the state of user 2*a* in FIG. 6), but also before and after heel 202 of user 2 leaves the ground (namely, the state of user 2*b* to user 2*c* in FIG. 6).

When the value detected by detection section 102 takes 180°, control section 103 determines that the walking motion of user 2 is in the foot contact phase and operates external stimulation section 101. Control section 103 sets the external stimulation time of external stimulation section 101 to 5 sec, for example. Alternatively, control section 103 compares the value detected by detection section 102 with a preset stop threshold (for example, 170°) at which the operation of external stimulation section 101 is to be stopped, and stops the operation of external stimulation section 101 when the detected value takes the stop threshold.

In Operation Example 1 described above, detection section 102 may detect not only the first information during the motion, but also the second information during the motion and the third information during the motion. Control section 103 may send one or more among the first information, the second information, and the third information during the motion, received from detection section 102, to storage section 105 or server 11. Control section 103 may send the information received from detection section 102 in real time or in bulk later.

In accordance with the information received from detection section 102, control section 103 may produce graphic data (see FIGS. 9A and 9B) and send the produced graphic data to external apparatus 4. The graphic data illustrated in FIG. 9A or 9B may be provided to external apparatus 4 or terminal 6, described later, by server 11.

Operation Example 2

Operation Example 2 of control section 103 in which the motion of user 2 is the walking motion and the target area is vastus medialis muscle 203 will be described below with reference to FIG. 6.

Also in this example, control section 103 controls external stimulation section 101 such that the external stimulus is applied to vastus medialis muscle 203 of user 2 in the foot contact phase of the walking motion.

In this example, detection section 102 detects the myoelectric potential in vastus medialis muscle 203 of user 2. In this example, therefore, first sensor 102a is a myoelectric sensor that measures the myoelectric potential in vastus medialis muscle 203.

More specifically, control section 103 compares the detected value (myoelectric potential in vastus medialis muscle 203), received from detection section 102, with the predetermined threshold. As illustrated in FIG. 6, vastus medialis muscle 203 of user 2 generates the higher myoelectric potential at the foot-contact phase start point (that is also the foot-off phase end point, the state of user 2a, 2f in FIG. 6) than in the other states during the walking motion.

When control section 103 compares the detected value with the predetermined threshold and determines that the walking motion of user 2 is in the foot contact phase, control section 103 operates external stimulation section 101 under the predetermined external stimulus condition. Prior to performing the above-described determination, control section 103 may execute a filtering process on the detected value to remove noise and a component caused by incidental and minute muscle activity that is not attributable to the walking motion of user 2.

Operation Example 3

Operation Example 3 of control section 103 in which the motion of user 2 is the walking motion and the target area is vastus medialis muscle 203 will be described below with reference to FIG. 6.

Also in this example, control section 103 controls external stimulation section 101 such that the external stimulus is applied to vastus medialis muscle 203 of user 2 in the foot contact phase of the walking motion.

In this example, detection section 102 detects a myoelectric potential in an area where the myoelectric potential is changed corresponding to vastus medialis muscle 203 during the walking motion of user 2. In this example, therefore, detection section 102 includes fourth sensor 102d (see FIG. 2) that detects the myoelectric potential in medial hamstring 206 or biceps femoris long head 207, for example.

As illustrated in FIG. 6, medial hamstring 206 and biceps femoris long head 207 generate the higher myoelectric potentials immediately before the foot-contact phase start point (that is also the foot-off phase end point, the state of user 2a, 2f in FIG. 2), at which vastus medialis muscle 203 generates the myoelectric potential, than in the other states during the walking motion.

Accordingly, control section 103 can determine that the walking motion of user 2 is in the state immediately before the foot contact phase, by comparing the detected value (namely, the myoelectric potential in medial hamstring 206 or biceps femoris long head 207) received from detection section 102 (fourth sensor 102d) with the predetermined threshold.

When control section 103 compares the detected value with the predetermined threshold and determines that the walking motion of user 2 is in the state immediate before the foot contact phase, control section 103 operates external stimulation section 101 under the predetermined external stimulus condition.

With the feature described above, since the state immediately before the myoelectric potential is generated in vastus medialis muscle 203 can be detected, the external stimulus can be efficiently applied to vastus medialis muscle 203 even when a delay occurs between the detection of the myoelectric potential and the application of the external stimulus.

Control section 103 may perform the above-described determination based on myoelectric potentials in a plurality of areas where the myoelectric potentials are changed corresponding to vastus medialis muscle 203 during the walking motion of user 2.

Operation Example 4

Operation Example 4 of control section 103 in which the motion of user 2 is the walking motion and the target area is vastus medialis muscle 203 will be described below with reference to FIG. 6.

In this example, control section 103 controls external stimulation section 101 such that the external stimulus is applied to vastus medialis muscle 203 of user 2 in the foot-off phase of the walking motion.

Also in this example, as in Operation Example 3 described above, detection section 102 detects a myoelectric potential in an area where the myoelectric potential is changed corresponding to vastus medialis muscle 203 during the walking motion of user 2. To that end, detection section 102 includes fifth sensor 102e that detects the myoelectric potential in gastrocnemius lateral head 208, for example.

As illustrated in FIG. 6, gastrocnemius lateral head 208 generates the higher myoelectric potential immediately before the foot-off phase start point (that is also the foot-contact phase end point, the state of user 2d in FIG. 2), at which vastus medialis muscle 203 generates the myoelectric potential, than in the other states during the walking motion.

Accordingly, control section 103 can determine that the walking motion of user 2 is in the state immediately before the foot-off phase, by comparing the detected value (namely, the myoelectric potential in gastrocnemius lateral head) received from detection section 102 (fifth sensor 102e) with the predetermined threshold.

When control section 103 compares the detected value with the predetermined threshold and determines that the walking motion of user 2 is in the state immediate before the foot-off phase, control section 103 operates external stimulation section 101 under the predetermined external stimulus condition.

With the feature described above, since the state immediately before the myoelectric potential is generated in vastus medialis muscle 203 can be detected, the external stimulus can be efficiently applied to vastus medialis muscle 203 even when a delay occurs between the detection of the myoelectric potential and the application of the external stimulus.

Operation Example 5

Operation Example 5 of control section 103 in which the motion of user 2 is a motion of standing from and sitting on a chair (hereinafter referred to as a "standing and sitting motion") and the target area is each of the back muscle (back), the rectus femoris muscle (thigh), and the tibialis anterior muscle (lower leg) will be described below with reference to FIG. 7. The standing and sitting motion is exercise not limited to the lower limb, namely whole body exercise, and the target areas can be set to the back muscle (back), the rectus femoris muscle (thigh), and the tibialis anterior muscle (lower leg) in which activity is especially intense.

Figure 7:
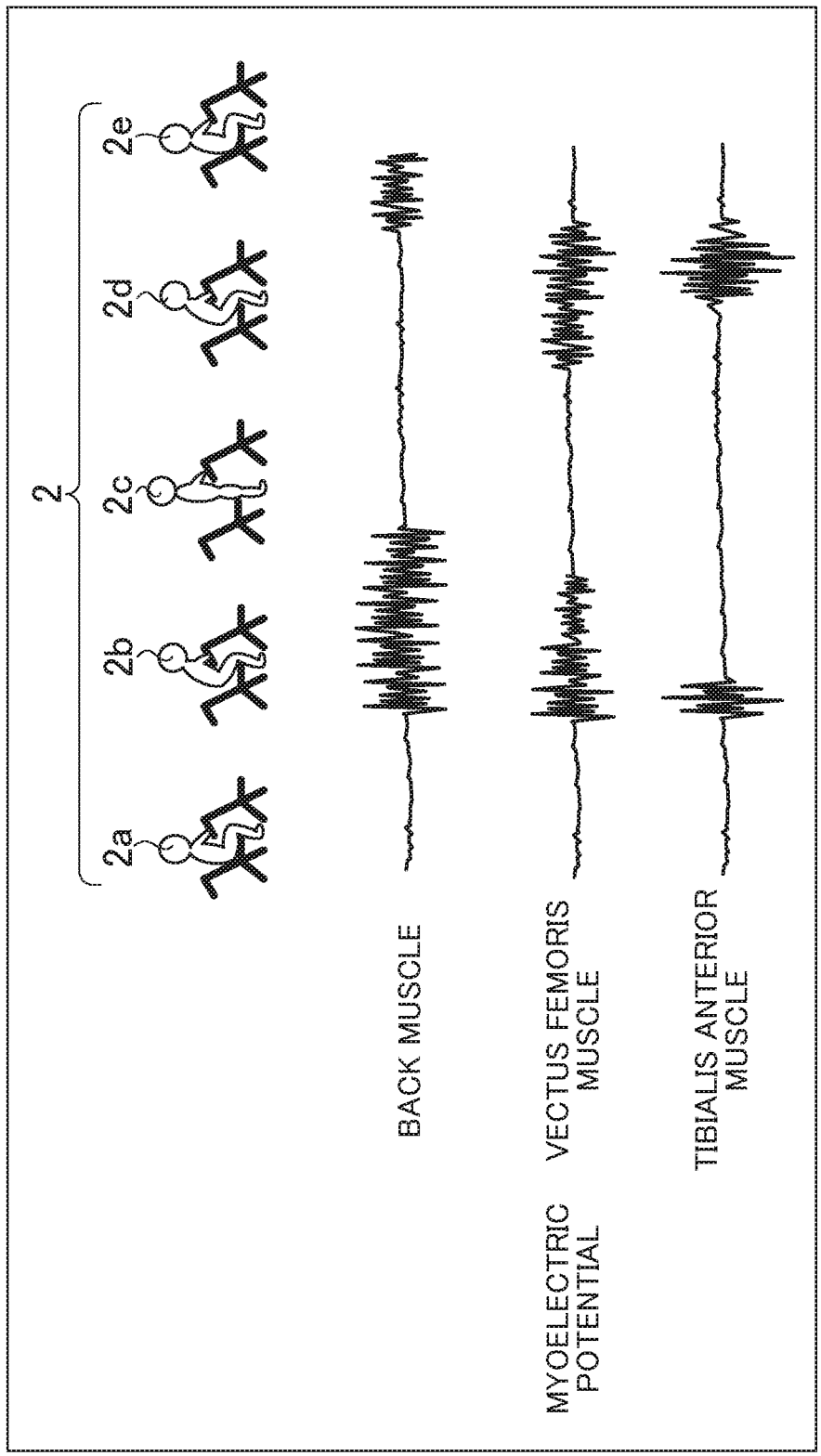
FIG. 7 illustrates changes in myoelectric potentials in various muscles during a motion of standing from and sitting on a chair.

As illustrated in FIG. 7, when standing up (namely, at transition from the state of user 2b to the state of user 2c in FIG. 7), the back muscle of user 2 generates the myoelectric potential during a period until reaching an upright position (see user 2c in FIG. 7) after the buttock has left the chair.

The tibialis anterior muscle generates the myoelectric potential in the state in which the angle of the ankle of user 2 is smaller than 90 degrees. The state in which the angle of the ankle of user 2 is smaller than 90 degrees is the state in which the buttock of user 2 is apart from the chair in FIG. 7 (namely, the state of user 2b in FIG. 7).

The rectus femoris muscle generates the myoelectric potential in the state in which user 2 lifts the body while turning the femoral region about the knee of the user. The state in which user 2 lifts the body while turning the femoral region about the knee of the user is the state until reaching the upright position (see user 2c in FIG. 7) from the state in which the buttock is apart from the chair in FIG. 7 (namely, the state of user 2b in FIG. 7).

On the other hand, in the sitting motion, the back muscle generates the myoelectric potential when user 2 readjusts, after the sitting, the state in which the trunk of user 2 is inclined (namely, the state of user 2e in FIG. 7).

In the sitting motion, the tibialis anterior muscle generates the myoelectric potential in the state in which the angle of the ankle of user 2 is smaller than 90 degrees. The state in which the angle of the ankle of user 2 is smaller than 90 degrees is the state immediately before the buttock reaches the chair (namely, immediately before the state of user 2e in FIG. 7).

In the sitting motion, the rectus femoris muscle generates the myoelectric potential in the state in which user 2 lowers the body while turning the femoral region about the knee of the user. The state in which user 2 lowers the body while turning the femoral region about the knee of the user is the state until the buttock reaches the chair (namely, until reaching the state of user 2e in FIG. 7) from the state in which user 2 has started the sitting motion (namely, from the state of user 2d in FIG. 7).

In this example, sensors (not illustrated) constituting detection section 102 are arranged at positions where the sensors can detect the myoelectric potentials in the target areas (namely, the back muscle, the tibialis anterior muscle, and the rectus femoris muscle). Control section 103 compares the detected value received from each of those sensors with the predetermined threshold, and determines whether the target area is being active. If the determination result indicates that the muscle in the target area is being active, control section 103 operates external stimulation section 101 under the predetermined external stimulus condition.

With the feature described above, the external stimulus from external stimulation section 101 can be efficiently applied to the target area of user 2 when the myoelectric potential is generated in the target area.

Among other motions in daily life, the motion using an upper limb is, for example, a motion of "lifting baggage". In this case, the target area is the biceps brachii muscle. The biceps brachii muscle is active mainly during a period in which the forearm is turned around the elbow.

<Communication Section>

Communication section 104 performs communication with external apparatus 4 described later. Communication section 104 is connected to the external apparatus via wireless communication such as WiFi (registered trademark, Wireless Fidelity), Bluetooth (registered trademark), wireless LAN, or NFC (Near Field Communication). As an alternative, communication section 104 may be connected to the external apparatus via network 5 such as the Internet.

Communication section 104 may perform mutual communication to synchronize the timing of applying the external stimulus between external stimulus application apparatus 10 worn on the right leg of user 2 and external stimulus application apparatus 10 worn on the left leg.

<Storage Section>

Storage section 105 stores information regarding the user (hereinafter referred to as "user information"). The user information includes not only age information, gender information, and exercise history information of the user, but also body information regarding the height and the weight of the user, and the muscle mass, the muscle density, and the subcutaneous fat per body area of the user. The user information may include information regarding a pain level in the target area of user 2. The user information may further include information regarding an instruction of a healthcare professional.

Storage section 105 stores information regarding the motion of the user. Moreover, storage section 105 stores, per user 2, information regarding the motion of the user, which have been performed in the past, in correspondence with the user information. Examples of the information regarding the motion of the user, which has been performed in the past, are the type of the exercise and the strength of the exercise.

Storage section 105 stores the external stimulus condition. When the external stimulus is the vibratory stimulus, the external stimulus condition includes, for example, the vibration amplitude, the vibration frequency, the vibration pattern, and the vibration mode of external stimulation section 101. Storage section 105 further stores the external stimulus condition of the external stimulus, which has been applied to the user in the past, in correspondence with both the user information and the information regarding the motion of the user when the external stimulus was applied.

When the external stimulus is the electrical stimulus, storage section 105 stores the electrical stimulus application condition. The electrical stimulus application condition includes, for example, not only the intensity (magnitude of the current output from the electrical stimulation section), the pulse, the frequency, the amplitude, the waveform (including a burst wave) of the electrical stimulus, but also the electrical stimulus application pattern and the electrical stimulus application mode.

When the external stimulus is the vibratory stimulus, the vibration pattern is not limited to a vibration in which the frequency, the amplitude, the vibration time, and so on are not changed, and includes a vibration in which at least one of the frequency, the amplitude, and the vibration time is changed. The term "vibration mode" represents one or more vibration patterns that are set in accordance with the purpose such as muscle training, rehabilitation, or pain relief. The vibration mode may be constituted by a combination of a plurality of vibration patterns. When the vibration mode includes a plurality of vibration patterns, the vibration patterns are switched from one to another at proper timing.

When the external stimulus is the electrical stimulus, the electrical stimulus application pattern is not limited to an electrical stimulus in which the pulse, the frequency, the amplitude, the waveform, the electrical stimulus application time, and so on are not changed, and includes an electrical stimulus in which at least one of the frequency, the amplitude, and the electrical stimulus application time is changed. The term "electrical stimulus application mode" represents one or more electrical stimulus application patterns that are set in accordance with the purpose such as muscle training, rehabilitation, or pain relief. The electrical stimulus application mode may be constituted by a combination of a plurality of electrical stimulus application patterns. When the electrical stimulus application mode includes a plurality of electrical stimulus application patterns, the electrical stimulus application patterns are switched from one to another at proper timing.

For example, the stimulus application mode may be set to apply a weak external stimulus for a certain period after start of the operation, and then to gradually increase the intensity of the external stimulus with the elapse of time. When the electrical stimulus is applied using a burst wave, for example, the stimulus application mode may be set to increase the frequency of the burst wave from 2 Hz to 20 Hz step by step.

Another example of the stimulus application mode may be set as follows. In the mode of this example, the frequency is first increased continuously or step by step from a first frequency to a second frequency that is higher than the first frequency. Next, the electrical stimulus with a burst wave at the second frequency (for example, 20 Hz) is continued for a predetermined time (for example, 20 minutes). After the lapse of the predetermined time, the frequency of the burst wave is reduced from 20 Hz to 2 Hz step by step, and the stimulus application is ended.

Storage section 105 stores the vibration condition and/or the electrical stimulus application condition in correspondence with the information regarding the motion of the user, which includes the type of the exercise and the strength of the exercise, and with items (such as the age, the gender, the height, and the weight of the user) included in the user information. Storage section 105 includes a vibration condition table (not illustrated) in which, for example, the vibration condition is stored in correspondence with the information regarding the motion of the user and the items included in the user information.

<Input Section>

Input section 106 obtains input information that is required to operate external stimulus application apparatus 10. Input section 106 receives the input information from external apparatus 4, such as a smartphone, through communication section 104. Input section 106 sends the received input information to control section 103. Input section 106 may obtain input information that is required to operate the electrical stimulation section (not illustrated).

When the external stimulus is the vibratory stimulus, the input information is, for example, information regarding ON/OFF switching of the power supply of external stimulus application apparatus 10, information regarding switching of the vibration frequency, and information regarding switching of the vibration pattern. The input information further includes various kinds of information that can be input from external apparatus 4 by user 2. The input information includes, for example, the vibration intensity, the weight, the height and the pain level of the user, and the instruction of the healthcare professional, which are input from external apparatus 4 by user 2.

Input section 106 may receive the information regarding the above-described vibration condition (for example, the vibration intensity) from external apparatus 4, such as the smartphone, through communication section 104. Input section 106 sends the received information to control section 103. Input section 106 may send the received information to storage section 105. Storage section 105 stores the information received from input section 106.

User 2 can input the above-described operating information and the information regarding the vibration condition by using an application installed in external apparatus 4.

When the external stimulus is the electrical stimulus, the input information may include, for example, information regarding ON/OFF switching of the power supply of external stimulus application apparatus 10, information regarding switching of the frequency of the electrical stimulus, and information regarding switching of the electrical stimulus pattern. Other items of the input information are similar to those in the case of the vibratory stimulus.

<Power Supply Section>

Power supply section 107 supplies power to the individual sections of external stimulus application apparatus 10. Power supply section 107 is held on wearing section 108 described below. Power supply section 107 is, for example, a chargeable battery or a dry cell. When power supply section 107 is chargeable, it may be charged by a contact or contactless method.

<Wearing Section>

Wearing section 108 is worn on the body of user 2 around the target area. In the body-worn state, wearing section 108 holds external stimulation section 101 at a suitable position with respect to the electrical stimulus applied surface. Furthermore, in the body-worn state, wearing section 108 holds detection section 102 at a suitable position with respect to the detected area. External stimulation section 101 held by wearing section 108 may be either the vibratory stimulation section or the electrical stimulation section.

Wearing section 108 has a shape like a supporter, for example. When wearing section 108 is in the form of a sleeve, the material of wearing section 108 is preferably an elastic material. More specifically, the elastic material is, for example, polyurethane, polyolefin-based elastomer, natural rubber, or silicone. Alternatively, wearing section 108 may have a strip shape like a bandage or a band. When wearing section 108 has the strip shape, the material of wearing section 108 is selected from various types of materials used in general supporters. More specifically, those materials are, for example, nylon, polyester, polyurethane, and cotton. Wearing section 108 may be formed of an adhesive member. The materials of wearing section 108 are not limited to the above-mentioned examples.

Wearing section 108 may include a position adjustment mechanism (for example, a sliding mechanism) that can adjust the position of external stimulation section 101.

Wearing section 108 may removably hold external stimulation section 101. In this case, wearing section 108 may include a larger number of holding portions (not illustrated), each of which holds external stimulation section 101, than external stimulation section 101. In such a case, user 2 selects one from among the plurality of holding portions, the one being used to hold external stimulation section 101.

By referring to FIG. 2 again, an example of the structure of wearing section 108 when the target area is vastus medialis muscle 203 of user 2 will be described below. Wearing section 108 has a shape like a substantially tubular supporter that is worn on leg 20 of user 2 over a range spanning from femoral region 204 to lower leg region 205.

Wearing section 108 includes a first holding portion 108a and second holding portion 108b. First holding portion 108a holds external stimulation section 101. First holding portion 108a is positioned to face vastus medialis muscle 203 of user 2 in the body-worn state.

First holding portion 108a may include a position adjustment mechanism (not illustrated) that can adjust the position of external stimulation section 101. The position adjustment mechanism is, for example, a sliding mechanism. First holding portion 108a may removably hold external stimulation section 101.

On the other hand, second holding portion 108b holds detection section 102. More specifically, second holding portion 108b includes holding portion element 108c and holding portion element 108d. Holding portion element 108c is arranged on the surface of femoral region 204 of user 2 in the body-worn state. Holding portion element 108c holds first sensor 102a of detection section 102.

Holding portion element 108d is arranged on the surface of lower leg region 205 of user 2 in the body-worn state. Holding portion element 108d holds second sensor 102b of detection section 102.

Wearing section 108 may include a tightening adjustment mechanism that can adjust tightening force in the body-worn state. The tightening adjustment mechanism is, for example, a belt-type adjustment mechanism. In this case, external stimulus application apparatus 10 may include a tightening determination section that determines whether the tightening force in the body-worn state is appropriate.

The tightening determination section can be constituted by a pressure sensor (not illustrated) and control section 103. The pressure sensor is held on wearing section 108. The pressure sensor detects information regarding the pressure between wearing section 108 and user 2. The pressure sensor sends the information regarding the detected pressure to control section 103.

Control section 103 determines, based on the information regarding the pressure and received from the pressure sensor, whether the tightening force is appropriate.

<Display Section>

External stimulus application apparatus 10 may include display section (not illustrated) that displays information regarding the status of external stimulus application apparatus 10. The display section displays, for example, the external stimulus condition and so on. For example, when external stimulus application apparatus 10 includes the electrical stimulation section, the display section may display the electrical stimulus application condition and so on.

<Server>

Server 11 (see FIG. 1) is an external server and is connected to external stimulus application apparatus 10 via network 5 such as the Internet, for example. Server 11 can further function as an external stimulus condition determination system and an external stimulus condition determination apparatus that send back the external stimulus condition in response to a request from external stimulus application apparatus 10.

When the external stimulus is the vibratory stimulus, server 11 can be regarded as a vibratory stimulus condition determination system and a vibratory stimulus condition determination apparatus that send back the vibratory stimulus condition in response to a request from external stimulus application apparatus 10. When the external stimulus is the electrical stimulus, server 11 can be regarded as an electrical stimulus condition determination system and an electrical stimulus condition determination apparatus that send back the electrical stimulus condition in response to a request from an electrical stimulus application apparatus (not illustrated). When the external stimulus application system includes both the vibratory stimulus application apparatus and the electrical stimulus application apparatus, server 11 can further functions as an external stimulus condition determination system and an external stimulus condition determination apparatus that send back the vibratory stimulus condition in response to a request from an external stimulus application apparatus (not illustrated). While the following description is made by taking external stimulus application apparatus 10 as an example, the "external stimulus" may be read as and replaced with the "vibratory stimulus" or the "electrical stimulus" as appropriate.

Server 11 includes server-side communication section 11a, server-side storage section 11b, and server-side control section 11c.

<Server-Side Communication Section>

Server-side communication section 11a is an interface connected to a communication apparatus (not illustrated), such as an antenna or a router, that is connected to network 5 such as a communication line (for example, the Internet) or a telephone line.

Server-side communication section 11a has the function of controlling communication between server 11 and external stimulus application apparatus 10. Server-side communication section 11a further has the function of controlling communication between server 11 and external apparatus 4. Server-side communication section 11a sends request information received from external stimulus application apparatus 10 or external apparatus 4 to server-side control section 11c.

Furthermore, server-side communication section 11a sends response information received from server-side control section 11c to a terminal (external stimulus application apparatus 10 or external apparatus 4) that has sent the request information.

<Server-Side Storage Section>

Server-side storage section 11b stores information regarding user 2 (hereinafter referred to as "user information"). The user information include not only age information, gender information, and exercise history information of the user, but also body information regarding the muscle mass, the muscle density, and the subcutaneous fat per body area of the user. The user information may include information regarding a pain level in the target area of user 2. The user information may further include information regarding an instruction of a healthcare professional. The user information stored in server-side storage section 11b is substantially similar to that stored in above-described storage section 105.

Server-side storage section 11b stores, peruser 2, information regarding the motion of the user. Server-side storage section 11b further stores, peruser 2, information regarding motion of the user, which has been performed in the past, in correspondence with the user information. Examples of the information regarding the motion of the user, which have been performed in the past, are the type of the exercise and the strength of the exercise. The information regarding the motion of the user, stored in server-side storage section 11*b*, is substantially similar to that stored in above-described storage section 105.

When the external stimulus is the vibratory stimulus, server-side storage section 11*b* stores the vibration condition of the vibratory stimulus. The vibration condition includes, for example, the vibration amplitude, the vibration frequency, the vibration pattern, and the vibration mode of vibratory stimulation section 101. Server-side storage section 11*b* further stores the vibration condition of the vibratory stimulus, which has been applied to the user in the past, in correspondence with both the user information and the information regarding the motion of the user. The vibration condition stored in server-side storage section 11*b* is substantially similar to that stored in above-described storage section 105.

Server-side storage section 11*b* stores the information detected by detection section 102. More specifically, server-side storage section 11*b* stores the first information during the motion, the second information during the motion, and the third information during the motion that have been detected by detection section 102.

Server-side storage section 11*b* stores a parameter that has been input by a server user, for example, a doctor, via terminal 6. As illustrated in FIG. 11B, for example, server-side storage section 11*b* stores the parameter in correspondence with the user information, the vibration conduction, the first information during the motion, the second information during the motion, the third information during the motion, and so on. The parameter will be described below later.

Server-side storage section 11*b* stores the external stimulus condition (for example, the vibration condition) in correspondence with the information regarding the motion of the user, which includes the type of the exercise and the strength of the exercise, and with items (such as the age, the gender, the height, and the weight of the user) included in the user information. Server-side storage section 11*b* includes an external stimulus condition table (for example, a vibration condition table not illustrated) in which, for example, the external stimulus condition (for example, the vibration condition) is stored in correspondence with the information regarding the motion of the user and the items included in the user information. The external stimulus condition table is also similar to that stored in above-described storage section 105.

In other words, server-side storage section 11*b* has a data structure including the external stimulus condition that is made in correspondence with the user information and the information regarding the motion. Such a data structure is used in processing executed by server 11 that is communicatively connected to external stimulus application apparatus 10. The processing executed by server 11 includes a step of receiving the user information and the information regarding the motion, a step of obtaining the external stimulus condition that corresponds to the user information and the information regarding the motion, which have been received in the above step, and a step of sending the obtained external stimulus condition to the external stimulus application apparatus. The above-mentioned data structure is stored in a recording medium, for example, server-side storage section 11*b*. The above-mentioned data structure may be presented in the state stored in a recording medium such as a DVD or a USB memory.

FIG. 11A is a conceptual view illustrating an example of a data structure D that is stored in server-side storage section 11*b* when the external stimulus is the vibratory stimulus. Data structure D includes the user information (specifically, the age and the gender), the information regarding the motion (specifically, the type of the exercise and the strength of the exercise), and the vibration condition (specifically, the vibration frequency).

In data structure D, the vibration condition is made in correspondence with the user information and the information regarding the motion. Thus, when the age, the gender, the type of the exercise, and the strength of the exercise are designated, the vibration condition is determined in accordance with data structure D. The configuration of the data structure is not limited to that illustrated in FIG. 11A. The items of the user information, the items of the motion, and the items of the vibration condition in data structure D are also not limited to those illustrated in FIG. 11A.

Server-side storage section 11*b* further includes a data structure in which the information (such as the first information, the second information, and the third information) during the motion of user 2, obtained from detection section 102, is made per user in correspondence with the parameter input by the healthcare professional. FIG. 11B is a conceptual view illustrating an example of such a data structure when the external stimulus is the vibratory stimulus.

FIG. 11C illustrates a table corresponding to that of FIG. 11A when the external stimulus is the electrical stimulus. FIG. 11D illustrates a table corresponding to that of FIG. 1B when the external stimulus is the electrical stimulus.

<Server-Side Control Section>

Server-side control section 11*c* receives, through server-side communication section 11*a*, the request information from external stimulus application apparatus 10 or external apparatus 4. The request information includes the user information and the information regarding the motion of the user.

Server-side control section 11*c* obtains, from server-side storage section 11*b*, the external stimulus condition (for example, the vibration condition) that corresponds to the items included in the received user information and the items included in the received information regarding the motion of the user. More specifically, server-side control section 11*c* sets a parameter in consideration of both the items included in the received user information and the items included in the received information regarding the motion of the user, and further obtains the external stimulus condition corresponding to the parameter from the external stimulus condition table in server-side storage section 11*b*. Then, server-side control section 11*c* sends the obtained external stimulus condition to server-side communication section 11*a*. Server-side control section 11*c* may be regarded as an external stimulus condition obtaining section.

In response to a request from the server user, for example, user 2 or the healthcare professional who can access server 11, server-side control section 11*c* may produce graphic data (see FIGS. 9A and 9B) based on the information from detection section 102 (for example, the second information during the motion), which is stored in server-side storage section 11*b*.

Server-side control section 11*c* sends the produced graphic data to a user terminal (terminal 6 communicatively connected to external stimulus application apparatus 10, external apparatus 4, or server 11) that is used by the server user. The graphic data is displayed on a display section of the user terminal (for example, display section 4*a* of external apparatus 4). The server user can view the graphic data displayed on the display section. When the server user is the healthcare professional, the healthcare professional can access server 11 from terminal 6, for example. The healthcare professional can check the effect of rehabilitation from the graphic data displayed on the display section (not illustrated) of terminal 6, and can set up an appropriate rehabilitation plan.

<External Apparatus>

External apparatus 4 is, for example, a computer, a smartphone, a wearable terminal, or a server. External apparatus 4 is connected to communication section 104 of external stimulus application apparatus 10. External apparatus 4 is connected to communication section 104 via wireless communication such WiFi, Bluetooth, wireless LAN, or NFC. Communication section 104 may be connected to the external apparatus via network 5 such as the Internet.

External apparatus 4 may be connected to server 11 via network 5 such as the Internet. In this case, external apparatus 4 is a terminal that is communicatively connected to server 11.

External apparatus 4 may send, as the request information, the user information and the information regarding the motion to server 11. The user information and the information regarding the motion may be input by user 2 through an input section (for example, a touch screen) of external apparatus 4. Alternatively, the user information and the information regarding the motion may be obtained from a storage section (not illustrated) of external apparatus 4 or storage section 105 of external stimulus application apparatus 10.

External apparatus 4 receives, from server 11, the external stimulus condition (the vibration condition or the electrical stimulus application condition) that corresponds to the request information. External apparatus 4 sends the received external stimulus condition to external stimulus application apparatus 10. Control section 103 of external stimulation section 101 sets the external stimulus condition, received from external apparatus 4, in external stimulation section 101.

External apparatus 4 further functions as a controller for external stimulus application apparatus 10. External apparatus 4 may include display section 4a.

Figure 10A:
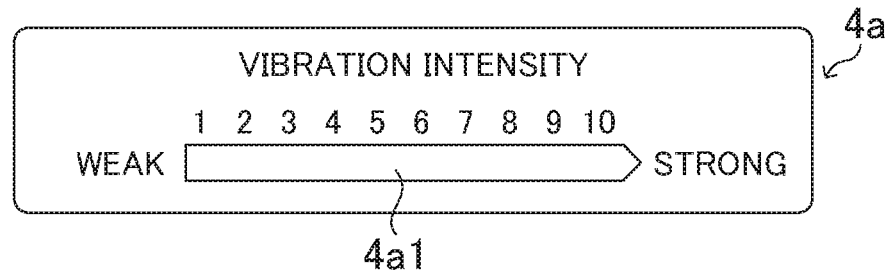
FIG. 10A illustrates Display Example 1 presented on a display section of an external apparatus.

FIG. 10A illustrates an example of an image displayed on display section 4a of external apparatus 4 when the external stimulus is the vibratory stimulus. As illustrated in FIG. 10A, for example, an intensity setting bar 4a1 for setting the vibration intensity is displayed on display section 4a of external apparatus 4. User 2 can set the vibration intensity, for example, by clicking the intensity setting bar 4a1. FIG. 10E illustrates an example of an image displayed on display section 4b of external apparatus 4 when the external stimulus is the electrical stimulus. As illustrated in FIG. 10E, an intensity setting bar 4b1 for setting the intensity (Hz) of the electrical stimulus is displayed on display section 4b. User 2 can set the intensity of the electrical stimulus, for example, by clicking the intensity setting bar 4b1. In FIG. 10E, the electrical stimulus of 4 Hz or higher and 8 Hz or lower is suitable when the strength of the exercise is low. In FIG. 10E, the electrical stimulus of 16 Hz or higher and 20 Hz or lower is suitable when the strength of the exercise is high.

External apparatus 4 sends information regarding the intensity of the external stimulus (namely, the intensity of the vibratory stimulus or the intensity of the electrical stimulus), which has been set using the intensity setting bar 4a1 or 4b1, to external stimulus application apparatus 10.

Figure 10B:
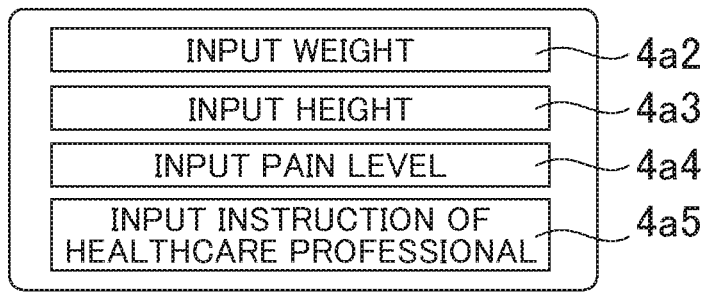
FIG. 10B illustrates Display Example 2 presented on the display section of the external apparatus.

Input icons 4a2 to 4a5 illustrated in FIG. 10B, byway of example, are displayed on display section 4a of external apparatus 4.

Input icon 4a2 is an icon to input the weight of the user. External apparatus 4 sends information regarding the input weight of user 2 to external stimulus application apparatus 10 or server 11.

Input icon 4a3 is an icon to input the height of the user. External apparatus 4 sends information regarding the input height of user 2 to external stimulus application apparatus 10 or server 11.

Input icon 4a4 is an icon to input the pain level of the user. External apparatus 4 sends information regarding the input pain level of user 2 to external stimulus application apparatus 10 or server 11.

Figure 10C:
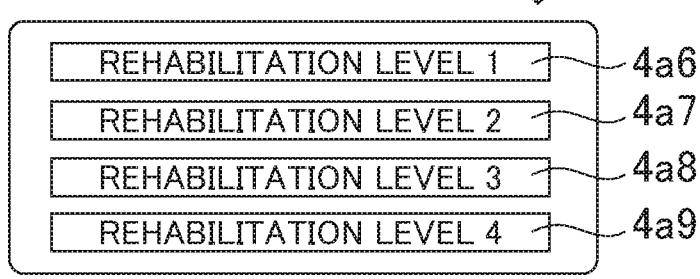
FIG. 10C illustrates Display Example 3 presented on the display section of the external apparatus.

Input icon 4a5 is an icon to input the instruction of the healthcare professional. For example, when user 2 clicks input icon 4a5 to input the instruction of the healthcare professional, selection icons 4a6 to 4a9 illustrated in FIG. 10C are displayed.

Selection icons 4a6 to 4a9 are icons to selectively set rehabilitation levels. User 2 clicks one of selection icons 4a6 to 4a9 and selects the rehabilitation level instructed by the healthcare professional. External apparatus 4 sends information regarding the input instruction of the healthcare professional to external stimulus application apparatus 10 or server 11.

Figure 10D:
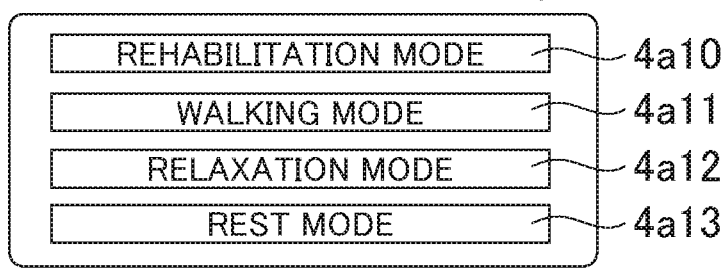
FIG. 10D illustrates Display Example 4 presented on the display section of the external apparatus.
Figure 10E:
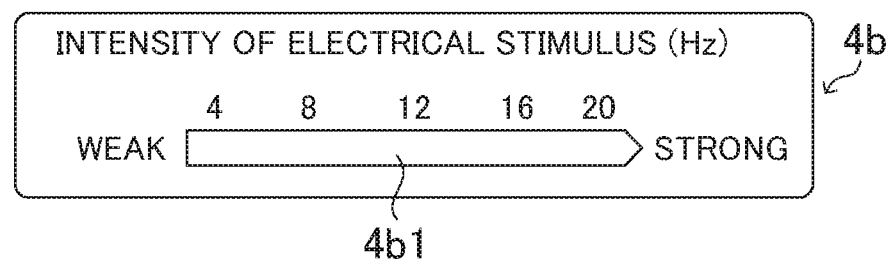
FIG. 10E illustrates Modification 1 of Display Example 1 illustrated in FIG. 10A.

When the external stimulus is the vibratory stimulus, selection icons 4a10 to 4a13 illustrated in FIG. 10D, by way of example, are displayed on display section 4a of external apparatus 4. Selection icons 4a10 to 4a13 are icons to selectively set the vibration modes. Selection icons 4a10 to 4a13 may be displayed when user 2 clicks the input icon 4a5 illustrated in FIG. 10B.

User 2 selects one of selection icons 4a10 to 4a13 corresponding to the favorite vibration mode or the vibration mode instructed by the healthcare professional. External apparatus 4 sends information regarding the vibration mode selected by user 2 to external stimulus application apparatus 10.

The types of icons are not limited to the above-described examples. User 2 can input, from external apparatus 4, various kinds of input information that are required to operate external stimulus application apparatus 10.

<Terminal>

The server user, for example, the healthcare professional, can access server 11 through terminal 6. Terminal 6 is, for example, a computer, a smartphone, or a wearable terminal. Terminal 6 may be connected to server 11 via network 5 such as the Internet.

The healthcare professional examines the symptom of user 2 (patient) based on the information (such as the first information, the second information, and the third information) during the motion of user 2, which is stored in server 11, and inputs a parameter in accordance with the diagnostic result from terminal 6.

The parameter may be, for example, one of stepwise parameters such as −2, −1, 0, +1, and +2. The parameter is not limited to such an example.

The parameter input by the healthcare professional will be described below, byway of example, in connection with the case in which the patient has injured the anterior cruciate ligament of the right knee. When the patient undergoes a reconstructive surgery for the anterior cruciate ligament of the knee, the patient performs proper rehabilitation before the surgery. After recovering to such a level as being able to live a daily life or to perform light exercise (usually after about two to four weeks from the injury), the patient undergoes the surgery. It is known that good recovery after the surgery is realized with the above-described care.

FIG. 11B illustrates an example of data stored in server-side storage section 11b when the patient having injured the anterior cruciate ligament of the right knee uses external stimulus application system 1 according to this embodiment. The data illustrated in FIG. 11B is data in the case in which the external stimulus is the vibratory stimulus. Such data may be data that can only be utilized by the patient and the healthcare professional.

A doctor examines the symptom of the patient based on the information (such as the first information, the second information, and the third information) during the motion of the patient, which is stored in server 11, and inputs the parameter in accordance with the diagnostic result. The parameter may be input per rehabilitation or at intervals of predetermined number of days. In the data structure illustrated in FIG. 11B, the parameter is input by the healthcare professional (doctor) per week from the first day after the injury.

For example, the doctor compares the recovery condition of the patient with statistical data (hereinafter referred to as a "comparative case") regarding the number of days elapsed after the injury and the recovery status in the same case, and sets "−2" as the parameter when the recovery degree of the patient is significantly delayed from that in the comparative case. When the recovery degree of the patient is slightly delayed from that in the comparative case, the doctor sets "−1" as the parameter. When the recovery degree of the patient is the same as that in the comparative case, the doctor sets "0" as the parameter. Furthermore, when the recovery degree of the patient is slightly advanced from that in the comparative case, the doctor sets "+1" as the parameter. When the recovery degree of user 2 is significantly advanced from that in the comparative case, the doctor sets "+2" as the parameter. The vibration condition and so on can be changed and set in accordance with the set parameter. For example, when the parameter "−1" is set, the vibration intensity is set to be 10% weaker or the vibration frequency in the vibration condition is set to be 10% lower in comparison with that when the parameter "0" is set.

The doctor may set the parameter in accordance with the condition (specifically, the muscle mass) of the patient's body. Also in this case, the doctor sets the parameter ranging from −2 to +2 per patient in accordance with the condition of the patient body. For example, when the muscle strength of the patient is naturally weak (when the muscle mass is small), the doctor sets "−1" as the parameter.

The doctor may set the parameter in accordance with the number of days required for the patient to recover. Also in this case, the doctor sets the parameter ranging from −2 to +2 per patient in accordance with the condition of the patient body. For example, when it is determined that the patient requires a larger number of days than usual, the doctor sets "−1" as the parameter.

When the patient has any disease, the doctor sets "−2" as the parameter. In this case, the doctor may set the parameter step by step in accordance with the condition of the patient's disease.

The doctor may set the parameter in accordance with the frequency at which the patient plays sports. Also in this case, the doctor sets the parameter ranging from −2 to +2 per patient in accordance with the frequency at which the patient plays sports. For example, when the patient is a person (for example, an athlete) who plays sports daily, the doctor sets "+1" as the parameter. The healthcare professional may set the parameter by making a comprehensive judgment on the above-described items.

Based on the information (such as the first information, the second information, and the third information) during the motion of the patient, which is stored in server 11, and the above-described parameter, the healthcare professional can assess the recovery degree of the patient's knee after the injury and determine the timing of the surgery.

Thus, the healthcare professional can present a more appropriate rehabilitation menu to user 2 based on the information (such as the first information, the second information, and the third information) during the motion of the patient, which is stored in server 11, and the above-described parameter. As a result, the healthcare professional can determine the proper timing of the surgery and support early return of the patient to daily life or competitions. FIG. 11D represents data in the case in which the external stimulus is the electrical stimulus. Doctor actions are similar to those described above with reference to FIG. 11B.

<Operation of External Stimulus Application System 1>

Figure 8:
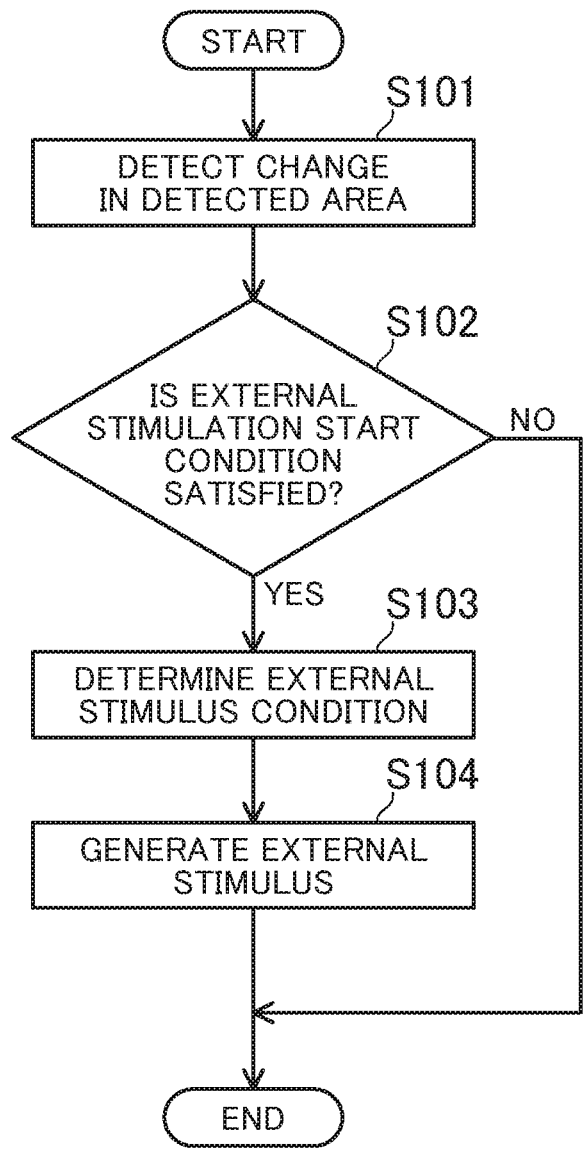
FIG. 8 is a flowchart referenced to explain an operation of the external stimulus application apparatus.

Operations of external stimulus application system 1 and external stimulus application apparatus 10 will be described below with reference to FIG. 8. FIG. 8 is a flowchart referenced to explain the operations of external stimulus application system 1 and external stimulus application apparatus 10 according to this embodiment. The following operations of external stimulus application system 1 and external stimulus application apparatus 10 can be read as operations of a vibratory stimulus application system and a vibratory stimulus application apparatus and operations of an electrical stimulus application system and an electrical stimulus application apparatus (those systems and apparatuses being all not illustrated) as appropriate.

In the following, duplicate description of the matters described above regarding the individual apparatuses constituting external stimulus application system 1 is omitted.

In step S101, detection section 102 detects change in the detected area of user 2 during the motion of user 2. Then, detection section 102 sends the detected value (physical quantity) to control section 103. Detection section 102 detects change in the detected area at intervals of a predetermined time and sends the detected value to control section 103.

In step S102, control section 103 compares the physical quantity received from detection section 102 with the predetermined threshold. In step S102, control section 103 further determines whether the comparison result satisfies the external stimulation start condition. For example, when the walking motion of user 2 is in the above-described foot contact phase, control section 103 determines that the external stimulation start condition is satisfied.

If it is determined in step S102 that the external stimulation start condition is not satisfied ("NO" in step S102), a control process illustrated in FIG. 8 is ended. The control process illustrated in FIG. 8 is repeatedly executed at intervals of a predetermined time.

On the other hand, if it is determined in step S102 that the external stimulation start condition is satisfied ("YES" in step S102), the control process shifts to step S103.

In step S103, control section 103 determines the external stimulus condition. For example, control section 103 obtains, from storage section 105 or server 11, the external stimulus condition stored therein.

Alternatively, in step S103, control section 103 may send request information including the user information and the information regarding the motion of the user, which has been input from input section 106, to server 11, and may obtain, from server 11, the external stimulus condition corresponding to the request information. The above-described steps are effective when the user uses external stimulus application apparatus 10 for the first time, or when the exercise performed by the user is new exercise. Furthermore, the above-described steps are effective when the user information (such as the weight, the muscle mass, or the subcutaneous fat) has greatly changed from the past user information. Thereafter, the control process shifts to step S104.

In step S104, control section 103 operates external stimulation section 101 in accordance with the external stimulus condition determined in step S103. As a result, the external stimulation is applied to the target area of user 2. The control process is thereby ended.

Operational Advantages of this Embodiment

According to this embodiment constituted as described above, the external stimulus can be applied to the user during the motion at the proper timing. In addition, since the information for checking the effect of rehabilitation can be detected and stored, the user or the healthcare professional can set up a treatment plan in accordance with the progress of the rehabilitation.

Embodiment 2

Figure 12:
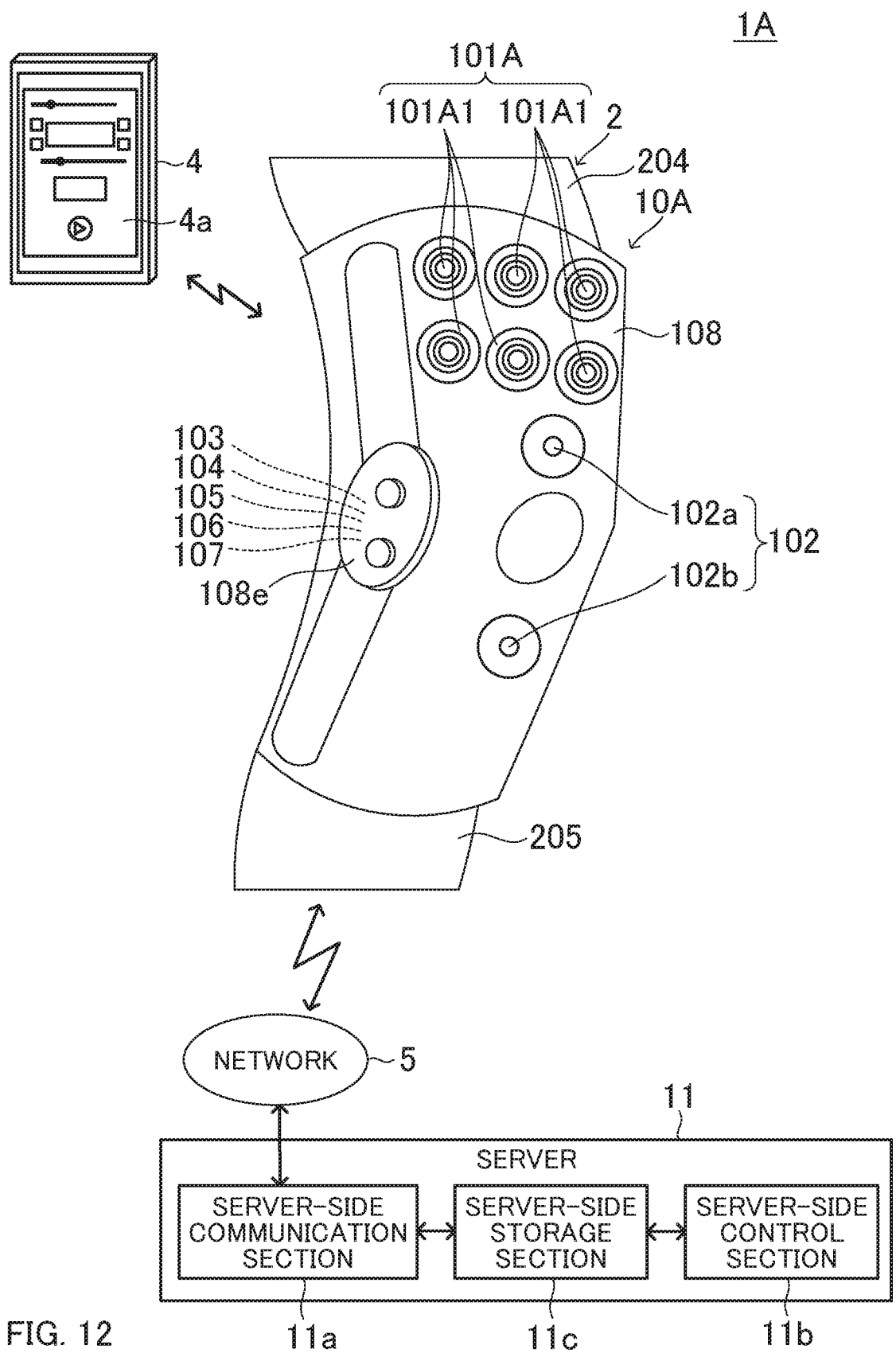
FIG. 12 illustrates an external stimulus application system according to Embodiment 2 of the present invention.

External stimulus application system 1A according to Embodiment 2 of the present invention will be described below with reference to FIG. 12. In external stimulus application system 1A, external stimulus application apparatus 10A has a structure different from that in above-described external stimulus application system 1 according to Embodiment 1. External stimulus application system 1A will be described below primarily about different points in structure from those in external stimulus application system 1.

External stimulus application apparatus 10A includes external stimulation section 101A, detection section 102, control section 103, communication section 104, storage section 105, input section 106, power supply section 107, and wearing section 108.

External stimulation section 101A includes a plurality (six in this embodiment) of external stimulation section elements 101A1. External stimulation section elements 101A1 are arranged on femoral region 204 of user 2 in the state held on wearing section 108.

Detection section 102 includes first sensor 102a and second sensor 102b. First sensor 102a is, for example, an acceleration sensor and is arranged in femoral region 204 of user 2 in the body-worn state. Second sensor 102b is an acceleration sensor and is arranged in lower leg region 205 of user 2 in the body-worn state. The configuration of detection section 102 is similar to that in Embodiment 1 described above.

Control section 103, communication section 104, storage section 105, input section 106, and power supply section 107 are held in hinge portion 108e of wearing section 108. The configurations of control section 103, communication section 104, storage section 105, input section 106, and power supply section 107 are similar to those in Embodiment 1 described above.

Wearing section 108 has a shape like a supporter that is wearable on the knee of user 2. The configuration of wearing section 108 is also substantially similar to that in Embodiment 1 described above. The other configurations, operations, and effects of external stimulus application apparatus 10A are similar to those in Embodiment 1 described above.

The disclosure of Japanese Patent Application No. 2018-068923, filed on Mar. 30, 2018, including the specification, drawings and abstract, is incorporated herein by reference in its entirety.

INDUSTRIAL APPLICABILITY

The external stimulus application apparatus according to the present invention can be further applied to motions of the user other than the walking, target areas of the user other than the vastus medialis muscle, and detected areas of the user other than the knee.

REFERENCE SIGNS LIST

1 External stimulus application system
10 External stimulus application apparatus
101, 101A to 101G External stimulation section
101a to 101g Housing
1011d, 1011g First housing element
1012d, 1012g Second housing element
1013d, 1013g Third housing element
1014d First joint section
1015d Second joint section
101m, 101n, 101p External stimulus transmission member
1011p First element
1012p Second element
1013p Third element
1014p First joint section
1015p Second joint section
101a1, 101b1, 101d1, 101d2, 101d3 External stimulus applying surface
101e1, 101f1, 101g1, 101g2, 101g3 External stimulus applying surface
101x1, 101x2, 101x3 Projection
101y1, 101y2 Flat surface region
102 Detection section
102a First sensor
102b Second sensor
102c Third sensor
102d Fourth sensor
102e Fifth sensor
103 Control section
104 Communication section
105 Storage section
106 Input section
107 Power supply section
108 Wearing section
108a First holding portion
108b Second holding portion
108c Holding portion element
108d Holding portion element
11 Server
12 Anti-vibration member
2, 2a to 2f User
20 Leg
201 Toe
202 Heel
203 Vastus medialis muscle
204 Femoral region
205 Lower leg region
206 Medial hamstring
207 Biceps femoris long head
208 Gastrocnemius lateral head
209 External stimulus applied surface 3 Ground
4 External apparatus
4a, 4b Display section
4a1, 4b1 Intensity setting bar
4a2 to 4a5 Input icon
5 Network
6 Terminal
D Data structure

What is claimed is:

1. An external stimulus application system, comprising:
an external stimulation section that applies an external stimulus to a target area in a body of a user;
a detection section that detects first information during a walking motion of the user, the first information being information regarding change in a detected area in the body of the user;
a control section that compares the first information with a threshold and causes the external stimulation section to generate the stimulus when the first information satisfies a predetermined condition; and
a storage section that stores a value detected by the detection section,
wherein:
the control section specifies, from a preceding cycle of the walking motion, a timing at which a foot of the user comes into contact with the ground, and updates the threshold based on the specified timing.

2. The external stimulus application system according to claim 1, wherein:
the detection section detects, together with the first information, second information that is information regarding the user during the motion other than the first information.

3. The external stimulus application system according to claim 2, wherein:
the second information includes at least one among items of information regarding a number of steps, a step length, a walking cycle, and a walking speed during walking or running of the user.

4. The external stimulus application system according to claim 1, wherein:
the control section determines, based on a comparison result between the first information and a predetermined threshold, whether the first information satisfies the predetermined condition.

5. The external stimulus application system according to claim 1, wherein:
when the motion of the user is a series of repeated motions that is performed by repeating a predetermined motion, the control section stores the timing of the stimulus that has been generated in the external stimulation section in the preceding predetermined motion in the series of repeated motions, and determines, based on the stored timing, timing of generating the stimulus in the external stimulation section.

6. The external stimulus application system according to claim 1, wherein:
the storage section includes an external server that is communicatively connected to the control section; and
the external server stores an external stimulus condition that is made in correspondence with user information regarding the user and information regarding the motion performed by the user.

7. The external stimulus application system according to claim 6, further comprising, an external apparatus that controls the external stimulation section, wherein:
the external apparatus receives, from the external server, the external stimulus condition corresponding to both the user information and the information regarding the motion, and sets the received external stimulus condition in the external stimulation section.

8. The external stimulus application system according to claim 6, wherein:
the external server is accessible from a terminal that is communicatively connected to the external server.

9. The external stimulus application system according to claim 6, wherein:
in response to a request from a terminal, the external server sends, to the terminal, information that is produced based on the detected value and that enables a treatment effect to be checked.

10. The external stimulus application system according to claim 1, wherein:
the motion of the user is walking or running.

11. The external stimulus application system according to claim 1, wherein:
the external stimulus application system includes a plurality of the external stimulation sections.

12. The external stimulus application system according to claim 1, wherein:
the detected value includes information regarding at least one among an acceleration, an angle, and a myoelectric potential in the detected area.

13. The external stimulus application system according to claim 12, wherein:
the detected area is a lower limb of the user.

14. The external stimulus application system according to claim 1, wherein:
the target area is a muscle of the user.

15. The external stimulus application system according to claim 14, wherein:
the muscle is a muscle in a femoral region of the user.

16. The external stimulus application system according to claim 1, wherein:
the external stimulus is a vibratory stimulus.

17. The external stimulus application system according to claim 1, wherein:
the external stimulus is an electrical stimulus.

* * * * *